United States Patent
Ma et al.

(10) Patent No.: US 11,390,877 B2
(45) Date of Patent: Jul. 19, 2022

(54) BLUE-GRAINED GENES IN WHEAT AND APPLICATION THEREOF

(71) Applicants: CAPITAL NORMAL UNIVERSITY, Beijing (CN); FRONTIER LABORATORIES OF SYSTEMS CROP DESIGN CO., LTD., Beijing (CN); PEKING UNIVERSITY INSTITUTE OF ADVANCED AGRICULTURAL SCIENCES, Shandong (CN)

(72) Inventors: Ligeng Ma, Beijing (CN); Zheng Wang, Beijing (CN); Zhuo Chen, Beijing (CN); Yanfang Heng, Beijing (CN); Xingwang Deng, Beijing (CN)

(73) Assignees: CAPITAL NORMAL UNIVERSITY, Beijing (CN); Beijing Next Generation Hybrid Wheat Biotechnology Co., Ltd, Beijing (CN); PEKING UNIVERSITY INSTITUTE OF ADVANCED AGRICULTURAL SCIENCES, Shandong (CN)

( * ) Notice: Subject to any disclaimer, the term of this patent is extended or adjusted under 35 U.S.C. 154(b) by 0 days.

(21) Appl. No.: 16/759,750

(22) PCT Filed: Nov. 8, 2017

(86) PCT No.: PCT/CN2017/109818
§ 371 (c)(1),
(2) Date: Apr. 28, 2020

(87) PCT Pub. No.: WO2019/090496
PCT Pub. Date: May 16, 2019

(65) Prior Publication Data
US 2021/0180075 A1 Jun. 17, 2021

(51) Int. Cl.
*C12N 15/82* (2006.01)
*C07K 14/415* (2006.01)

(52) U.S. Cl.
CPC .......... *C12N 15/825* (2013.01); *C07K 14/415* (2013.01)

(58) Field of Classification Search
None
See application file for complete search history.

(56) References Cited

FOREIGN PATENT DOCUMENTS

| CN | 101935663 A | 1/2011 |
|---|---|---|
| CN | 103695460 A | 4/2014 |
| CN | 104774251 A | 7/2015 |
| WO | 2009061214 A1 | 5/2009 |

OTHER PUBLICATIONS

Li et al., 2017, PLoS ONE, 12:1-13.*
Toledo-Ortiz et al., 2003, The Plant Cell, 15:1749-1770.*
Predicted: *Aegilops tauschii* subsp tauschii transcription factor MYB114-like (LOC109740355), mRNA. Genbank ID: XM_020299403.1. Genbank. Feb. 24, 2017(Feb. 24, 2017). The FEATURES and ORIGIN parts.
Li,N. et al. Thinopyrum ponticum MYC4E (MYC4E) mRNA, complete cds Genbank ID: KX914905.1. Genbank. Jul. 23, 2017(Jul. 23, 2017). The FEATURES and ORIGIN parts.
Predicted: *Aegilops tauschii* subsp tauschii anthocyanin regulatory R-S protein-like (LOC109740362), mRNA. Genbank ID: XM_020299413.1. Genbank. Feb. 24, 2017(Feb. 24, 2017). The FEATURES and ORIGIN parts.
Transcription factor MYB114-like *Aegilops tauschii* subsp tauschii. Genbank ID: XP_020154992 1. Genbank. Feb. 24, 2017(Feb. 24, 2017). The FEATURES and ORIGIN parts.
Li,N. et al. MYC4E Thinopyrum ponticum. Genbank ID: ASL69970. 1. Genbank. Jul. 23, 2017(Jul. 23, 2017). The FEATURES and ORIGIN parts.
Pireyre, M. et al. Regulation of MYB and bHLH Transcription Factors: A Glance at the Protein Level Molecular Plant. Mar. 31, 2015(Mar. 31, 2015), vol. 8, pp. 378-388.
Shi, M. Z. et al. Biosynthesis and Metabolic Engineering of Anthocyanins in *Arabidopsis thaliana*. Recent Patents on Biotechnology. Dec. 31, 2014(Dec. 31, 2014), 8(1), pp. 47-60.
Schwinn KE et al., "MYB and bHLH transcription factor transgenes increase anthocyanin pigmentation in petunia and isianthus plants, and the petunia phenotypes are strongly enhanced under field conditions", Frontiers in Plant Science, 5, Article 603, https://doi.org/10.3389/fpls.2014.00603, Nov. 5, 2014 (Nov. 5, 2014).
First examination report of corresponding CA application No. 3,080,642.

* cited by examiner

*Primary Examiner* — Jason Deveau Rosen
(74) *Attorney, Agent, or Firm* — Gang Yu

(57) ABSTRACT

The disclosure discloses blue-grained genes in wheat and use thereof, and belongs to the fields of plant molecular biology, biochemistry, genetics and plant breeding. The disclosure is capable of, through using differential expression analysis of blue-grained and white-grained wheat, obtaining four genes for controlling wheat blue-grained trait: two MYB family transcription factors and two bHLH family transcription factors, and providing a plant recombinant expression vector of the above genes and a method for controlling plant anthocyanin synthesis, and has important theoretical and practical significance to research a synthetic pathway of blue-grained wheat aleurone layer pigment, serve as a screening marker in a plant transformation process and improve a nutritional value of a plant.

6 Claims, 3 Drawing Sheets

Specification includes a Sequence Listing.

SEQUENCE LISTING

<160> NUMBER OF SEQ ID NOS: 20

<210> SEQ ID NO 1
<211> LENGTH: 822
<212> TYPE: DNA
<213> ORGANISM: Elytrigia elongata

<400> SEQUENCE: 1

```
atggcgaagg aagggtgaa gagagggca tggactggca aggaggacga aaccttggct      60
tcctacgtca aggcgcatgg cgaaggcaga tggaacgaag tccctcagag agctggtaag    120
tccctagcta ggtaaacaga atcaatctag agaatggagt gctaaacgta atttacaggt   180
cttcggcggt gcggcaagag ctgtcggctg cggtggctga actacctccg gccgaacatc   240
aagcggggaa acatatccaa tgatgaggag gagatcatcg tcaggctcca cgctctcctt   300
ggcaacaggt ggtcgctcat cgctggcagg ttgcctggcc gaacagacaa cgaaatcaag   360
aactactgga acagcaccct tggccggaag gtgcttcccg caccacattc cgccaccagg   420
atggttgcca cgccagacac ctccgccggc tccggatctt acaaagaggc gtcggcaagt   480
ctgtcaagct ctggacctgg tacaagcgac aaggctgcga cgccgtcgcc gctgccggcc   540
acgctgtggg cgccaaagcc tgtgaggcac acggggcacc ccttcttcct ccgggatagg   600
ccgccgccct tgccggttgc ggagacgcga accgtggcca acggggatgc ctgcagcggc   660
agcagctcgg tgacatcgga gttcccggct gtaccgccct cgttaggcag cgacgactgg   720
atggacgaag tgagagcctt ggaatcgttt ctcgagtccg acgaagactg ggtaaactct   780
gtggagatgc caacgcccaa ctctcacaca tcatcgagtt aa                      822
```

<210> SEQ ID NO 2
<211> LENGTH: 759
<212> TYPE: DNA
<213> ORGANISM: Elytrigia elongata

<400> SEQUENCE: 2

```
atggcgaagg aagggtgaa gagagggca tggactggca aggaggacga aaccttggct      60
tcctacgtca aggcgcatgg cgaaggcaga tggaacgaag tccctcagag agctggtctt   120
cggcggtgcg gcaagagctg tcggctgcgg tggctgaact acctccggcc gaacatcaag   180
```

```
cggggaaaca tatccaatga tgaggaggag atcatcgtca ggctccacgc tctccttggc    240
aacaggtggt cgctcatcgc tggcaggttg cctggccgaa cagacaacga aatcaagaac    300
tactggaaca gcacccttgg ccggaaggtg cttcccgcac acattccgc caccaggatg    360 gttgccacgc cagacacctc cgccggctcc ggatcttaca aagaggcgtc ggcaagtctg    420
tcaagctctg gacctggtac aagcgacaag gctgcgacgc cgtcgccgct gccggccacg    480
ctgtgggcgc caaagcctgt gaggcacacg gggcacccct tcttcctccg ggataggccg    540
ccgcccttgc cggttgcgga cgcgaacc gtggccaacg gggatgcctg cagcggcagc      600
agctcggtga catcggagtt cccggctgta ccgccctcgt taggcagcga cgactggatg    660
gacgaagtga gagccttgga atcgtttctc gagtccgacg aagactgggt aaactctgtg    720
gagatgccaa cgcccaactc tcacacatca tcgagttaa                           759
```

```
<210> SEQ ID NO 3
<211> LENGTH: 252
<212> TYPE: PRT
<213> ORGANISM: Elytrigia elongata

<400> SEQUENCE: 3

Met Ala Lys Glu Gly Val Lys Arg Gly Ala Trp Thr Gly Lys Glu Asp
1               5                   10                  15

Glu Thr Leu Ala Ser Tyr Val Lys Ala His Gly Glu Gly Arg Trp Asn
            20                  25                  30

Glu Val Pro Gln Arg Ala Gly Leu Arg Arg Cys Gly Lys Ser Cys Arg
        35                  40                  45

Leu Arg Trp Leu Asn Tyr Leu Arg Pro Asn Ile Lys Arg Gly Asn Ile
    50                  55                  60

Ser Asn Asp Glu Glu Ile Ile Val Arg Leu His Ala Leu Leu Gly
65                  70                  75                  80

Asn Arg Trp Ser Leu Ile Ala Gly Arg Leu Pro Gly Arg Thr Asp Asn
                85                  90                  95

Glu Ile Lys Asn Tyr Trp Asn Ser Thr Leu Gly Arg Lys Val Leu Pro
            100                 105                 110

Ala Pro His Ser Ala Thr Arg Met Val Ala Thr Pro Asp Thr Ser Ala
        115                 120                 125

Gly Ser Gly Ser Tyr Lys Glu Ala Ser Ala Ser Leu Ser Ser Ser Gly
    130                 135                 140

Pro Gly Thr Ser Asp Lys Ala Ala Thr Pro Ser Pro Leu Pro Ala Thr
145                 150                 155                 160

Leu Trp Ala Pro Lys Pro Val Arg His Thr Gly His Pro Phe Phe Leu
                165                 170                 175

Arg Asp Arg Pro Pro Leu Pro Val Ala Glu Thr Arg Thr Val Ala
            180                 185                 190

Asn Gly Asp Ala Cys Ser Gly Ser Ser Val Thr Ser Glu Phe Pro
        195                 200                 205

Ala Val Pro Pro Ser Leu Gly Ser Asp Asp Trp Met Asp Glu Val Arg
210                 215                 220

Ala Leu Glu Ser Phe Leu Glu Ser Asp Glu Asp Trp Val Asn Ser Val
225                 230                 235                 240

Glu Met Pro Thr Pro Asn Ser His Thr Ser Ser Ser
                245                 250

<210> SEQ ID NO 4
```

```
<211> LENGTH: 798
<212> TYPE: DNA
<213> ORGANISM: Elytrigia elongata

<400> SEQUENCE: 4
atggcgaagg aagtggtgaa gagaggggca tggactggca aggaggacga aaccttggct    60
tcctacgtca aggcgcatgg cgaaggcaga tggaacgaag tcccccaaag agctggtaag   120
tccctagctg gtaaacagaa tcaatctag acaatggagt gctaaacgta atttacaggt   180
cttcggcggc gcggcaagag ctgtcggctg cggtggctga actacctccg ccgaacatc   240
aagcggggaa acatatcaaa cgatgaggag gagatcatcg tcaggctcca cgctctcctt   300
ggcaacaggt ggtcgctcat cgctggcagg ttgcccggcc gaacagacaa cgaaatcaag   360
aactactgga cagcaccct ggccggaag gtgcttcccg caccacattc cgccaccagg    420
atggttgcca cgccagacac ctccgccgcc tccggatctt acacagaggc gtcggcaagt   480
ctatctagct ctggacctgg tacaagcgac aaggctgcga cgccgtcgcc gctcccggcc   540
acgctgtggg cgccaaagcc tgtgaggtac acggccacc ccttcttcct ccgggatagg    600
ccgcggccct tgccggttgc ggagacgcga accgtggcca cggggatgc ctacagcggc    660
agcagctcgg tgacatcgga gttcccggct gtcccgccct cgttaggcag tgacgactgg   720
atggacgaag taagagcctt ggaatcgttt ctcgagtccg acgaagactg gtaaactct    780
gtggagatgc cggattaa                                                  798

<210> SEQ ID NO 5
<211> LENGTH: 735
<212> TYPE: DNA
<213> ORGANISM: Elytrigia elongata

<400> SEQUENCE: 5
atggcgaagg aagtggtgaa gagaggggca tggactggca aggaggacga aaccttggct    60
tcctacgtca aggcgcatgg cgaaggcaga tggaacgaag tcccccaaag agctggtctt   120
cggcggcgcg gcaagagctg tcggctgcgg tggctgaact acctccggcc gaacatcaag   180
cggggaaaca tatcaaacga tgaggaggag atcatcgtca ggctccacgc tctccttggc   240
aacaggtggt cgctcatcgc tggcaggttg cccggccgaa cagacaacga atcaagaac   300
tactggaaca gcaccttgg ccggaaggtg cttcccgcac cacattccgc caccaggatg    360
gttgccacgc cagacacctc cgccgcctcc ggatcttaca cagaggcgtc ggcaagtcta   420
tctagctctg gacctggtac aagcgacaag gctgcgacgc cgtcgccgct cccggccacg   480
ctgtgggcgc caaagcctgt gaggtacacg gccacccct tcttcctccg ggataggccg    540
cggcccttgc cggttgcgga gacgcgaacc gtggccaacg gggatgccta cagcggcagc   600
agctcggtga catcggagtt cccggctgtc ccgccctcgt taggcagtga cgactggatg   660
gacgaagtaa gagccttgga atcgtttctc gagtccgacg aagactgggt aaactctgtg   720
gagatgccgg attaa                                                    735

<210> SEQ ID NO 6
<211> LENGTH: 244
<212> TYPE: PRT
<213> ORGANISM: Elytrigia elongata

<400> SEQUENCE: 6

Met Ala Lys Glu Val Val Lys Arg Gly Ala Trp Thr Gly Lys Glu Asp
1               5                   10                  15
```

```
Glu Thr Leu Ala Ser Tyr Val Lys Ala His Gly Glu Gly Arg Trp Asn
             20                  25                  30
Glu Val Pro Gln Arg Ala Gly Leu Arg Arg Gly Lys Ser Cys Arg
         35                  40                  45
Leu Arg Trp Leu Asn Tyr Leu Arg Pro Asn Ile Lys Arg Gly Asn Ile
 50                      55                  60
Ser Asn Asp Glu Glu Glu Ile Ile Val Arg Leu His Ala Leu Leu Gly
 65                  70                  75                  80
Asn Arg Trp Ser Leu Ile Ala Gly Arg Leu Pro Gly Arg Thr Asp Asn
                 85                  90                  95
Glu Ile Lys Asn Tyr Trp Asn Ser Thr Leu Gly Arg Lys Val Leu Pro
             100                 105                 110
Ala Pro His Ser Ala Thr Arg Met Val Ala Thr Pro Asp Thr Ser Ala
         115                 120                 125
Ala Ser Gly Ser Tyr Thr Glu Ala Ser Ala Ser Leu Ser Ser Ser Gly
     130                 135                 140
Pro Gly Thr Ser Asp Lys Ala Ala Thr Pro Ser Pro Leu Pro Ala Thr
145                 150                 155                 160
Leu Trp Ala Pro Lys Pro Val Arg Tyr Thr Gly His Pro Phe Phe Leu
                 165                 170                 175
Arg Asp Arg Pro Arg Pro Leu Pro Val Ala Glu Thr Arg Thr Val Ala
             180                 185                 190
Asn Gly Asp Ala Tyr Ser Gly Ser Ser Val Thr Ser Glu Phe Pro
         195                 200                 205
Ala Val Pro Pro Ser Leu Gly Ser Asp Asp Trp Met Asp Glu Val Arg
     210                 215                 220
Ala Leu Glu Ser Phe Leu Glu Ser Asp Glu Asp Trp Val Asn Ser Val
225                 230                 235                 240
Glu Met Pro Asp

<210> SEQ ID NO 7
<211> LENGTH: 12351
<212> TYPE: DNA
<213> ORGANISM: Elytrigia elongata

<400> SEQUENCE: 7
atggcgctat cagctcctcc cagtcaggaa cagccgtcgg ggaagcaatt cggctaccag      60
ctcgctgctg ctgtgaggag catcaactgg acttatggca tattttggtc catttccgcc     120
agcccgcgcc aggccactc ctcgtaatga ataaatgacc actctctatc tctatattat     180
gtatcatatt tgggtttgta gcaaacccac aaaattccta cttttcatat atatagtgtc     240
cgtcgtcgac gccgccggtt cgttttgcag agttctggcg tggaaggatg gttctacaa     300 cggcgagata aagactagaa agattaccgg ctcgaccact acggagctta cagcggacga     360
gcgcgtcatg cacagaagca agcaactgag ggagctctac gaatcgctct tgcccggcaa     420
ctccaacaac cgggcaaggc gaccaaccgc ctcactgtca ccgaggatc tcggggacgg     480 cgagtggtat tacaccataa gcatgactta caccttccac cctaatcaag ggtacgtact     540
tatcaaccat gatggatgtg atatatgtgc ctgccatgtt tcataccgtc catattttta     600
tatacgggta cattttttt tttgcgggtt tatatacggg tacatgacaa agacaattt     660 tgcggttagt tatcttgtta atatatactg tcatgttgcc gccaggaaaa gatcacttca     720
agaaaattat aaacaaacat atataatacg tccaattatt ttcagccttt cctttttt     780 aaattaaata catgagtcc aagcttcaaa tcctgcactt aaacctcaag ctaatctgtt     840
```

```
acactcccct gcagctagtc tcttactagt attatctctt cttctttttt tagaaaaact    900
ttcgatctat tcatcatgac agtaaaaaaa aaacactaga aataacaaaa attacattca    960
tatttataga acacctagcg acgattgcaa acattcaact gtgcgccgaa ggcgcactac   1020
actcatcgcc ccttcctggt tggagttggg caaacttcat tgtagtagac ggtaggaaag   1080
tctttgtgct aaggccttaa aggaccagca caccatgaca acaaccatca tcattaaaga   1140
aaagcatagg tcgaaaggat tcaacaagta gacacataac acaggaaaac taaggccgaa   1200
tccaggtata tccattgaag tcaaacactg accgaatccc gcgagattca ccgacatgcc   1260
ctccgacaat gctagatgca tcaacgggat agggactttt ttttagaaag gaggattacc   1320
cccggcttct gcatctggga gatgcatgca gccattgtat taattattca caaagacctt   1380
acaaaatagt acatcaggta gtctgaagcc atcatcttat caacaactgt cgctactcct   1440
atccacttga tgaaatggtg ccgatagtcc gagcctaata ccagacagac atcgcaccaa   1500
agcctaacat ctaaagccga gggcccaacc aaacgggata gggacttggc agggtgaacc   1560
ttattttatc ttcagagagc agagcgttgc ctcacggcct catcttcctg agcagcacac   1620
aaacactaaa taaaactaaa aaaactctta aaatgaagta ggagccctct cgccggcaag   1680
agccgggatc catcataccc ccatggccct aaagccgaag gaggcgagga agctcgacgg   1740
cagcgtcggt gggaggcgaa aagccctcgt ttcctgggag ttcgtcgtg gagcactaat    1800
actatcttga tactagctac cgtagactgc agtgttaaga tgtacatact gaagtgattt   1860
ttttctgtcg gcgtgaatgt acttactgcc aggttgccag gcaaaagctt tgcgagcaat   1920
caacatgttt ggctgtacaa cgctcaatac gcaaacacca gagttttccc ccgcgcgctc   1980
ttagcaaagg tatatctatt ctacagtact tatctattat gtgtgtatag caatgatgcg   2040
ggtcgggttt tcaacctcct tttctgaaat aagaaaacat cgtttggtct ttaactaata   2100
ataataatac tccaaaacgt gcatgatgtt gcccacacat ccgatggtca aatcagactg   2160
cttctattca ggtcagcaca ttacttccta ttatagatag atgggataca tacattttc    2220
gtccttaaat tcttgtgaaa gtttacaaat cgtccctcaa ctcaaaacca tcaaaattca   2280
aaactcagtc cctcaactat taaaaccgga tatttttcgt ccttgataac gcttcaggcg   2340
gttttagtct gacatggaca ccggttttga ctaatatcgg ccacgtggcc tgggtttgac   2400
catcacgtca gtcagttaag tgactaaagg acctcctgtc gaagagaata aagggcagta   2460
tggcgcaggg ccatgcagct tcaggttcga tccaggtcac ctagttcttg tcatagatga   2520
cgttcgagca gtccaccagc gtagggaagc acgactgcgc cgccagcggg tgcagaagtc   2580
gaagggcgac ttgggccgcg gctgccgcag ggtctgacgt tagtcggtag caagtgctcg   2640
aagtcgaagg gcggcaggag gaaaccgatg ccggcgccgt cgccgacctg ccactcggcc   2700
ttggcgctgg tgaggacgga ggcatgcacc aagctcagga ggacggaggc gtccatggcg   2760
cctagcccat gtcacggtgc gccatggccg cgagctcggc cggcctcctg caccacagcc   2820
gtgtatgccc aaggccgcag cctcgcttgt gcgcgctcgt gcagcccac gcgcttcctc    2880
ctcgtccgct cccccatgcc cggccgtgct ccgagcgagc acccaccgcg ccctggccct   2940
gtcccgtgcc tgcgcaaccg cgtgttgacc ggccattgcc aggtgggccg accagtttac   3000
ttagctgatg gttttgacca ccagactaaa accgggccac atcggcagca tttgtcaaaa   3060
ccgggtatcc atgtcagact aaaaccgccc aaaactttac gaaggacgaa aaatattcag   3120
ttttaatagt tgagggactg agtttttgatg gttttaaagt tgagggataa tttataaact   3180
```

```
ttgacagaag tttaaggacg aaaaatatac ttatccctag atagatacat agacgcacac    3240
atatacacat ctctgatctc aaaccgttca cattttttcca gacaatcgtt tgcattccct    3300
tcatgggcgg tgtgcttgag ctcggaacgt cggatcaggt cggtgcacat gagtttcaat    3360
ttatgttctc agtaactctc agcatgtttc tccgacttgc cgacgggttc aacggtaacc    3420
ttttaatatt aggggtagct attttgtgtg ccaatacatg ctactagcta ttttttgtatg   3480 tgttgtccca gtctaccatt ctgccccttt gcatttatgg cgttattcct ttctagtaca    3540
ttaatttaca ctagtcttcc actgcgtttt tctactacta cgtatttttat actatacttg   3600 tgattatctt tagagcaagt ataatagagt gatgtaggca ggctataaga gatgtcacat    3660
cagattatgc ctagttggag gagagagaaa atgagagaga aagaagcag gttacaagct     3720 tacggtcggc tgtagcacga gactcaacaa ccttttgtgtg tgagagggt gggccatata    3780 ttaattgtat gacaaactag tatgactagc tattgtacga gtgggctatt aggctgacta    3840
taagtgacat gacaactcta tatagacggc tcttggctat actattaacc atgctcttac    3900
ctctctcccg ccgccatgat gagagcctca ccggccctgt tactgggtca agggagacca    3960
acgcccaccg agcccgacca atcttgcagc ccacaccact acgtcaccct agcaactccg    4020
ctagtagccc gtcacctagg cacaatgact tcaacacctc gagagcaagc gccctgtcgc    4080
ggagccaccg tgctcgcaca tgtcgggatc tctcccacct tcgaagaggc aaggggggcgc   4140 aacccatcat aatcctacgg cggcagcggc ggccaggttg ggcattggag ggggtgctgc    4200
ttagcatcgg agacatggtg tcgcctagtg gtacgacacg acccggagag gaaaacagaa    4260
aacattgcga gcgcaagttc gccacgagtg ttgcgtgtta ttttttactaa ataacccttg   4320 aggatcttat ttttgtccac tgccccccaaa acgtatttcg tggcctgacc cctacgacca   4380
cgccaaataa tctggcgttt tagatacact agatgccacc ggtcaatctg acagcaataa    4440
attcaatgtg acagtggcgc ctacatgaca agaaaagtca aaagccaaat ttgaaggcct    4500
atatcatccg ataaaatctc cggttagtat ggcggggcat gctgcttcct tcttcctctg    4560
cacgaaccct gcgaggccac cggccaccgc caccgctggt agcagccggc tccagccacg    4620
gtagaggggc cctgcggtgg aggaagtcga cgggccggtg catgctctcc gccactgccg    4680
tgaccaccag catgaccgcc tcctcgtcct cgtccaccgc cgcgaccggc gtcgagcacg    4740
gggccgacgc gtcgtctgac gtattcccgc gcctctggaa ctctgaggtt ggggccacct    4800
tccgccgcac gtccgtggac ccggcggcac gcgacgagtc cgcggcacgg gaaggggcac    4860
tctcagcagc ggcgccatttt ccaccgcatg gggacgactc atcggtggtg aggtcgccgc    4920
cggcacgctt cgacgcaagc agctcgagcg tcgagtccac attaacgcca ttgcacgaat    4980
ctgtagacgg tccctccacg ccgagtccga gcgcgcgccc gtcagccctt ccgcccgacc    5040
ccgtccaagt ccccattggt ggggcaagca actgcttggc cggtgctccc aacagcgagg    5100
atgacctcca cctagctcgg acgcgacgtc gccggccacc actgtaagat atggccgggg    5160
aagtagctgc cttatcgaag gagcccgcgg cggaccagtg gcagtgtggt gcaccgggac    5220
caacagaggg gggcagataa ccaaataagt ttttttgagga gttagtgcac gaaataagat    5280
cctttagagt caattagtaa attaacacat tgttaatttt attaattctc gtattaatttt   5340 tactaattga cacgagtgtc ttcctaaaaa aaaaatttaa cacgagtgtt gcaccgcgac    5400
gtgcaaccaa ccgtttgatt gcttctcgtt gccgtgagta tgcttgtgaa cgtcgctcgt    5460
aacgtgccac gggctaacgt ttgcactcca ccatctgtta acctttgatt accatttttt    5520
acggggtaaa acattgcatt actcaagagg aataagttct tcgctgcaga gagtagtagg    5580
```

```
gtcgtttaca agacctgaac atatgtgtgc tgtcatgcaa cactttattt attaggttgt   5640
agacttatct tgtcttgata tgtgtgatgt tacaataact agctatgtta caacatgccc   5700
ctctttcctc attaattagt cgccacatca tctgttttgc ctacagatgt gtgatgttac   5760
cacctatgtt actcccacta tgggtagtct tattgtgatt agcaccggtg tgccaacact   5820
tagtcccttt ccatgaggaa cccctcccag acggcctcat tgaaggatat ttgtccgtct   5880
tgtactcaat ggtgacgggc cctgctcaag ccgtacacca acaaggccta tccgcgggat   5940
gttcaggccg gaaatcacat tcataagtaa tttcgaatct ctcccgtgga ttaaaataaa   6000
aaagagcaca caatgttagg catcgccata tagtgttatg cacaaaaaaa aggaatacta   6060
aaaaacgtac catagcatgt gtgacgatgt ttgtcttagt caaaaggtgc ataaagggca   6120
cccccgtgta gtcatcagcg ggtgatagga tgtcgaagag attggtggtc tcatctcagt   6180
aagcatcttc attctttcag agaaatatgc agaatataat ggatcatcct tctgatgctc   6240
gttgatatac ataatccttg atctagggac ttccttcaag aaaaaacata tatcctatcc   6300
gccgatgagc ccattgtttg aaaggaactt atcccatcct tggactttga atggccgctc   6360
atcagcattc ttaaagagca gagtgtcaca tgttgcatcg ttgaactcca ccctaacgtt   6420
gcatgggata cactatgcaa caatagagaa aaatgcagta aataattatt ggtaaagata   6480
ctaaaataag tgcaattgtg tgctaaagtt aaagaatatt accacggatt attcgaattc   6540
ctcattcaag taaagaccgg atgacactcc agataacatg ctgtttgcgc ggtcagattt   6600
ctagatttgg cacatcatcc tgttacgttt tctttagagg aggatcatcc ccggcctctg   6660
catctgatcg atgcatgcat ccattttatt aattattcac caaagacctt acaaagaaat   6720
acaacaataa gtctcaagtc atcgtctatg cgacaactgt cgctactcct atccagctga   6780
tgaagggatg ctgatagtcc gggcctaata ccacagacct cgcagacaag cctaacatct   6840
aagacctgag gccccaacca agccacttgc cgggtatggg cacacaccgg tccgcgcgc   6900 tctcagatgc cgccgccgcc aactgccact actccatctt cagagctgta ctgacgcatc   6960
attcttgccc ggtctagctg tcgtcaacgc caccacgacg cccaatggca ccaccaccct   7020
gtgcgcaaac tgctgagcac gtcgcggtcg ccgccggtac acctcagcac catgccgcca   7080
agtaccatca gtcgacacag cttgaagtct ctgggagatc tgtcatgcgt agcacctgcc   7140
aaccatgcat gacaaagcgt agtagtgtta cgtgcatgac ttattttatc cctacgaaca   7200 tttttcccaaa atttattcac gtgtagctta aaacaacata atttctaagt atttgcctct   7260
atacaatcaa tatcaccaac acctatcaag caaaagtcaa acttgacgtt gcaagtgcac   7320
ccctgcagta aatatttgac atactagttt atcaaattaa tatttgagaa catctaagct   7380
cgcagcgaag aggccgagga cataaaaagg tcttcgccag aaaaaatcag catggttttt   7440
gctaaaaagt tgaacatatt gagtgccaaa aaagttgtcg aaagagaaat taatcacatt   7500
ttgcctgaac attcatgaat ccctgaattt ttgaaaatgg aagaattctg aatacctaca   7560
ctatttaatc caaagggggtc aattaagacc tacattgcta aacgaaccaa tacatatata   7620
tcagacacaa acttgatttt tatgtaatag aaaggtccat gcgaacctta aactcgactt   7680
gtaacagaaa cttcccagcg aggttttgac cctaaccctc tccaggactt gtgtgtcgta   7740
gacgacacat ccacaggtga ggaaattaaa cgcctggctt ctggattcta catggaaatg   7800
tgatcatcta tggtgatata cgaatgcgtg cagtgtgcgt gaacggggtg gtgtgcaagg   7860
aaccgaagac catggtggtg ggaaacgtct tctttgtcag cgaggacagg cccggcaacg   7920
```

```
cggacaaaaa ccgctatgtg ttcttggtgc tgaacatgca gagcccaggc ttgaacacgc     7980
tactcctggt ggcggcgcgg ttcatacatc tagcgagaga caggacgagc agcaagggga     8040
gagggacggg tggcttatgt accaacgatt aagtaggaac taaggcagat ccggcgacgg     8100
gcgcctgcgg tggagcgacg gtgcggtccg atggcgaagg atttggatgg gtccagggtt     8160
tggatttggg gggtaatgtt caggaatgac gaagggttat gcctgcacgc caagacttag     8220
aagtcgcagc ctcccatgcg acatcacagg ccctccagtt atgcatattc acagtgtcgg     8280
gcaattttag gtgcctgcca caactaatat tttgccaatt tctggtaata atcttaaatt     8340
ttttctttat tttaggacta tatttctgtt ctcctttctt tgtggggttt aaagtaactt     8400
cttagaaact cccatgcccg aatttgggac taatctattt tttctttgtt attttttaaag    8460
cattaaatga gtttctagcc actaaaatga gcaaaatgct cattgcttcg aaaaaagagg     8520
caaatgagca ctgaaaagga tgaaccttgg catgtgttca ttatatgact cctataggct     8580
gtgctaaaaa tctgagaacg ttatgggcaa acgtgatgc acttcattta caaactgaac      8640
actcttggat aaagtatcag gctttcggat ggaaacctt gcctcccata gagaattctt      8700
tctccttcga acttttttac ttcatttccc cttgaacgtt ttcgatgtca aaacatacac     8760
aactgcaagt ctcatgctca aatttgagac tactctaggt tggtttgcta attttaaagc     8820
attaactgca tttctaacca cttaaatgag caaaattctc ttcgattcat aaccacatac     8880
acatgagtta taaaaatgat gaaacttgga atgggttcat tatatgattt ctacaaggtg     8940
tggtataaat tttagagcgt tacgggagaa acatgatgca ctttgtgtac aaactgaact     9000
ctctcaaatg aagtatcgga ttttcaaacg gaaacgttgg acttccacat agaacttaat     9060
tcttgtgcat catttccctt caaactttt ctatatttaa tatacatagt aaaagtctc      9120
atgatcaaaa tggggactat tcttggttga tttgctattt ttaaagtatt aaatgatttt    9180
ctagctatta aaaggagcaa aatgctctta cattcaaaat aaggtgcaaa taagctttaa    9240
aaaggataaa tgtggcaagg attcattata tgacacatat aggcagtggt aaaatttgaa    9300
aagcgttacg ggataaactt aatgcacttc ttctacaaaa tgaacactct ccgaagaagc    9360
atcagggttc tgaacggaaa ccttggactt caacaaagaa ctcaattttg ttaaatcatt    9420
tcccttttaa accttttat atgtttaata cacacagtta aaagtctcat gatcaaatgt     9480
ggtactattc tgggttgatt tgctattttt aaggcattaa gggccagtta ttttttggcgg   9540
tttagaaaag taagttgact ctccccagct taaataataa gtcatcttct aaatttgtaa    9600
ggcttctaaa acaagttatc ccataactag tgtagaagcc ccaacgaata agagaggtgg    9660
ttatgaaaaa agctggggaa aaggtggctt attttctatg ttgccgtcaa ttattttcta    9720
cccattaaga ggttcagaat gcccttgat tcaaaataat atgaaatgag ctctaaaagc    9780
gatgaaactt ggcatggttc ataatatgac ccctacagg gtgtgcggac aaaaataatt     9840
aagagcgtta cgcgaaaaac ttgatgcact tcgtgtataa actgaacact ctgtgacgaa     9900
gtatcaggat ttcgaacgca aatctttgac ttactcatag aattcaattt ttttatatca     9960
tttccacttc aaactgtatg tttaatatac acaactgaaa ctcccatgct caaatttggg    10020
actattctgg gttaattaat atgattttt ttcaaaaaat ttccttactt attagatcta     10080
cggtgggatc cttttgtgc cagccgctgc tatctttga attttttaga aaattttgac      10140
gtcgcttagc gaaatattgc taaggtgggc accttactgc ccgtcattgg tatttcacaa    10200
accaatgacg gaccgtagtt tgttgcccat cactgctgtt tttgtttcac gactaatttt    10260
gcaaaactgt acgagtggcg cgtgtccaat ttgcccacca ctgatgttcg tatagcatgg    10320
```

```
caggccacgt ttatcacccg ccactcgtac tataccaaaa tagcaatgac gggttccaga      10380
cctcaccttc cactaaagtg accccaccta tatataagcc ttttaaccag tagtgtatct      10440
ggctctcaca cacacatact ctaggttcct cttaacacaa aatctctctt cctccctaca     10500
cacagtctat ccatctctct ctagatgtat gcccacatag gtgggtgact gccgtcgtcg      10560
acgcggatag ggtttgggat tgacatctca cgggagagag acaaggggga caagatattt      10620
acaccactgg ccgggaatcc actagtttta tttgagagtt gagactattc gatgacgagt      10680
gtgtccagtg ggctttctgg cagtgcctgc ttttctctct ttcccgtccc atgtataact      10740
ctattctgag ttgtattttt gttatcagta acgggaaggg tatacccggt taaaagaaaa      10800
ggctgtattt ggtgaggtat atgtttgtat agtgggaaaa tgataatata tgggtagcgg      10860
ccggacgcat cttgagttct tgacgacaga ttccttacca gtacctacta ccgttagcgg      10920
taaaaatgcc tttgcgagta gctaccacgt taacacttgg cccagtcttt cctttcgtcg      10980
tcgtcagtcc acgtaaaaga aatgctattg aaaattgaca aagtgttatc cctgtatttc      11040
caaggtgttg gaggacccga gcatggtgaa gcggatcagc acgtctttct gggagctgca      11100
cttgccgtca tccttggagt cgaaggatcc gagctccagc acatcagcaa acgataccag      11160
ggaggccacc gacatcatct tgttcgagga tttcgaccac aacgacacag ttgaggggt      11220 gatctctgag caaagggagg tccagtgccc gtccaacgtc aatctggagc gcctcacaaa      11280
gcagatggac gagttccaca gccttctcgg tggactggac gtgcatcctc tcgaagacag      11340
atggatcatg gacgagccct ttgagtttac gttttcccca gaagtggcgc cggctatgga      11400
tatgccgagc accgacgatg tcatcgtcac tttaagtagg tccgaaggct ctcgtccatc      11460
ctgcttcaca gcgtggaagg gatcatccga gtcgaaatac gtggctggcc aggtcgttgg      11520
ggagtcacag aagttgctga ataaagttgt ggctggtggt gcatgggcga gcaattatgg      11580
cggtcgcacc atggtgagag ctcagggaat taacagcaac acccatgtca tgacagagag      11640
aagacgccgg gagaaactca acgagatgtt cctggttctc aagtcactgg tcccgtccat      11700
tcacaaggta gtaatatgta aagtccatgt acctttagca aactgcacac gttgttttc      11760 atagcttttt tactgttgga ttgcaggtag acaaagcatc catcctcaca gaaacgatag      11820
gttatcttag agaactgaag caaagggtag atcagctaga atccagccgg tcaccgtctc      11880
acccaaaaga aacaacagga ccgagcagaa gccatgtcgt cggcgctagg aagaagatag      11940
tctcggccgg atccaagagg aaggcgccag ggctggagag cccgagcaat gtcgtgaacg      12000
tgacgatgct ggacaaggtg gtgctgttgg aggtgcagtg cccgtggaag gagctgctga      12060
tgacacaagt gtttgacgcc atcaagagcc tctgtctgga cgttgtctcc gtgcaggcat      12120
ccacatcagg tggccgtctt gacctcaaga tacgagctaa tcagcaggta tatatagatc      12180
gcactaattt ctacgaccga tctggcagta tataaggaaa tgtatagcct gacttaagga      12240
tccatgatta ccgtctcatt cactgacatt gctggattgt tgcagcttgc ggtcggttct      12300
gctatggtgg cacctggggc aatcaccgaa acacttcaga aagctatata g              12351
```

<210> SEQ ID NO 8
<211> LENGTH: 1683
<212> TYPE: DNA
<213> ORGANISM: Elytrigia elongata

<400> SEQUENCE: 8

```
atggcgctat cagctcctcc cagtcaggaa cagccgtcgg ggaagcaatt cggctaccag      60
```

-continued

```
ctcgctgctg ctgtgaggag catcaactgg acttatggca tattttggtc catttccgcc    120
agcccgcgcc caggccactc ctcagttctg gcgtggaagg atgggttcta caacggcgag    180
ataaagacta gaaagattac cggctcgacc actacggagc ttacagcgga cgagcgcgtc    240
atgcacagaa gcaagcaact gagggagctc tacgaatcgc tcttgcccgg caactccaac    300
aaccgggcaa ggcgaccaac cgcctcactg tcaccggagg atctcgggga cggcgagtgg    360
tattacacca taagcatgac ttacaccttc caccctaatc aagggttgcc aggcaaaagc    420
tttgcgagca atcaacatgt ttggctgtac aacgctcaat acgcaaacac cagagttttc    480
ccccgcgcgc tcttagcaaa gactgcttct attcagacaa tcgtttgcat tcccttcatg    540
ggcggtgtgc ttgagctcgg aacgtcggat caggtgttgg aggacccgag catggtgaag    600
cggatcagca cgtctttctg ggagctgcac ttgccgtcat ccttggagtc gaaggatccg    660
agctccagca catcagcaaa cgataccagg gaggccaccg acatcatctt gttcgaggat    720
ttcgaccaca acgacacagt tgaggggtg atctctgagc aaagggaggt ccagtgcccg    780
tccaacgtca atctggagcg cctcacaaag cagatggacg agttccacag ccttctcggt    840
ggactggacg tgcatcctct cgaagacaga tggatcatgg acgagccctt tgagtttacg    900
ttttccccag aagtggcgcc ggctatggat atgccgagca ccgacgatgt catcgtcact    960
ttaagtaggt ccgaaggctc tcgtccatcc tgcttcacag cgtggaaggg atcatccgag   1020
tcgaaatacg tggctggcca ggtcgttggg gagtcacaga agttgctgaa taagttgtg    1080 gctggtggtg catgggcgag caattatggc ggtcgcacca tggtgagagc tcagggaatt   1140
aacagcaaca cccatgtcat gacagagaga agacgccggg agaaactcaa cgagatgttc   1200
ctggttctca gtcactggt cccgtccatt cacaaggtag acaaagcatc catcctcaca   1260
gaaacgatag ttatcttag agaactgaag caaagggtag atcagctaga atccagccgg   1320
tcaccgtctc acccaaaaga acaacagga ccgagcagaa gccatgtcgt cggcgctagg   1380
aagaagatag tctcggccgg atccaagagg aaggcgccag ggctggagag cccgagcaat   1440
gtcgtgaacg tgacgatgct ggacaaggtg gtgctgttgg aggtgcagtg cccgtggaag   1500
gagctgctga tgcacaaagt gtttgacgcc atcaagagcc tctgtctgga cgttgtctcc   1560
gtgcaggcat ccacatcagg tggccgtctt gacctcaaga tacgagctaa tcagcagctt   1620
gcggtcggtt ctgctatggt ggcacctggg gcaatcaccg aaacacttca gaaagctata   1680
tag                                                                 1683
```

<210> SEQ ID NO 9
<211> LENGTH: 560
<212> TYPE: PRT
<213> ORGANISM: Elytrigia elongata

<400> SEQUENCE: 9

```
Met Ala Leu Ser Ala Pro Pro Ser Gln Glu Gln Pro Ser Gly Lys Gln
1               5                   10                  15

Phe Gly Tyr Gln Leu Ala Ala Ala Val Arg Ser Ile Asn Trp Thr Tyr
            20                  25                  30

Gly Ile Phe Trp Ser Ile Ser Ala Ser Pro Arg Pro Gly His Ser Ser
        35                  40                  45

Val Leu Ala Trp Lys Asp Gly Phe Tyr Asn Gly Glu Ile Lys Thr Arg
    50                  55                  60

Lys Ile Thr Gly Ser Thr Thr Thr Glu Leu Thr Ala Asp Glu Arg Val
65                  70                  75                  80
```

-continued

```
Met His Arg Ser Lys Gln Leu Arg Glu Leu Tyr Glu Ser Leu Leu Pro
                85                  90                  95

Gly Asn Ser Asn Asn Arg Ala Arg Arg Pro Thr Ala Ser Leu Ser Pro
            100                 105                 110

Glu Asp Leu Gly Asp Gly Glu Trp Tyr Tyr Thr Ile Ser Met Thr Tyr
        115                 120                 125

Thr Phe His Pro Asn Gln Gly Leu Pro Gly Lys Ser Phe Ala Ser Asn
    130                 135                 140

Gln His Val Trp Leu Tyr Asn Ala Gln Tyr Ala Asn Thr Arg Val Phe
145                 150                 155                 160

Pro Arg Ala Leu Leu Ala Lys Thr Ala Ser Ile Gln Thr Ile Val Cys
                165                 170                 175

Ile Pro Phe Met Gly Gly Val Leu Glu Leu Gly Thr Ser Asp Gln Val
            180                 185                 190

Leu Glu Asp Pro Ser Met Val Lys Arg Ile Ser Thr Ser Phe Trp Glu
        195                 200                 205

Leu His Leu Pro Ser Ser Leu Glu Ser Lys Asp Pro Ser Ser Ser Thr
    210                 215                 220

Ser Ala Asn Asp Thr Arg Glu Ala Thr Asp Ile Ile Leu Phe Glu Asp
225                 230                 235                 240

Phe Asp His Asn Asp Thr Val Glu Gly Val Ile Ser Glu Gln Arg Glu
                245                 250                 255

Val Gln Cys Pro Ser Asn Val Asn Leu Glu Arg Leu Thr Lys Gln Met
            260                 265                 270

Asp Glu Phe His Ser Leu Leu Gly Gly Leu Asp Val His Pro Leu Glu
        275                 280                 285

Asp Arg Trp Ile Met Asp Glu Pro Phe Glu Phe Thr Phe Ser Pro Glu
    290                 295                 300

Val Ala Pro Ala Met Asp Met Pro Ser Thr Asp Asp Val Ile Val Thr
305                 310                 315                 320

Leu Ser Arg Ser Glu Gly Ser Arg Pro Ser Cys Phe Thr Ala Trp Lys
                325                 330                 335

Gly Ser Ser Glu Ser Lys Tyr Val Ala Gly Gln Val Val Gly Glu Ser
            340                 345                 350

Gln Lys Leu Leu Asn Lys Val Val Ala Gly Ala Trp Ala Ser Asn
        355                 360                 365

Tyr Gly Gly Arg Thr Met Val Arg Ala Gln Gly Ile Asn Ser Asn Thr
    370                 375                 380

His Val Met Thr Glu Arg Arg Arg Glu Lys Leu Asn Glu Met Phe
385                 390                 395                 400

Leu Val Leu Lys Ser Leu Val Pro Ser Ile His Lys Val Asp Lys Ala
                405                 410                 415

Ser Ile Leu Thr Glu Thr Ile Gly Tyr Leu Arg Glu Leu Lys Gln Arg
            420                 425                 430

Val Asp Gln Leu Glu Ser Ser Arg Ser Pro Ser His Pro Lys Glu Thr
        435                 440                 445

Thr Gly Pro Ser Arg Ser His Val Val Gly Ala Arg Lys Lys Ile Val
    450                 455                 460

Ser Ala Gly Ser Lys Arg Lys Ala Pro Gly Leu Glu Ser Pro Ser Asn
465                 470                 475                 480

Val Val Asn Val Thr Met Leu Asp Lys Val Val Leu Leu Glu Val Gln
                485                 490                 495

Cys Pro Trp Lys Glu Leu Leu Met Thr Gln Val Phe Asp Ala Ile Lys
```

```
                     500                 505                 510
    Ser Leu Cys Leu Asp Val Val Ser Val Gln Ala Ser Thr Ser Gly Gly
                 515                 520                 525

Arg Leu Asp Leu Lys Ile Arg Ala Asn Gln Gln Leu Ala Val Gly Ser
             530                 535                 540

Ala Met Val Ala Pro Gly Ala Ile Thr Glu Thr Leu Gln Lys Ala Ile
    545                 550                 555                 560

<210> SEQ ID NO 10
<211> LENGTH: 4003
<212> TYPE: DNA
<213> ORGANISM: Elytrigia elongata

<400> SEQUENCE: 10
atggcgctat cagctcctcc cagtcaggaa cagccgtcgg ggaagcaatt cggctaccag      60
ctcgctgctg ctgtgaggag catcaactgg acgtatgcca tattttggtc catttccgcc     120
agcccgcgcc caggccactc tcgtaatga ataaatgacc actctctatc tctatatgta     180
tcaatagata tcatatttgg gtttgtagca aacccacaaa gttcgtactt tcatatata     240 tagtgtccgg cgtcgacgcc gtcggttcgt ttcgcagagt tctggcgtgg aaggatgggt     300
tctacaacgg cgagataaag acaagaaaga ttaccggctc gaccactacg gagcttacag     360
cggacgagcg cgtcatgcac agaagcaagc aactgaggga gctctacgaa tcgctcttgc     420
ccggcaactc caacaatcgg gcaaggcgac ctgccgcctc actgtcaccg gaggatctag     480
gggacggcga gtggtattac accataagca tgacttacac cttccaccct aatcaagggt     540
acgtagttat caaccatgat gtatgcgata tatgtgcctg ccatgattca tgccgtccat     600 attttatat acgggtacat gacaaagaca aattttgcgg ttatgaaaat agtcacaaac     660
atgcactatt ttttgttaca aattacatat taatttgtac cttttttagt agttatcttg     720
ttaatatata ctggcatgtt gttgccagga aaagatcact tcaagaaaat tataaacaag     780
catatataat acgtccatac atatgtccaa ttattttcag ccttttcctt tttctaaatt     840
aaatacatag agtccaagct tcaaatcctg cacttaaacc tcaagctaat ctgttacact     900
cccttgcagc tagtctctta ctagtattat ctgttctttt tttgaaggaa aaactttcga     960
tctattcgtc atcatcacag taaaaaaaac actagaagta acataaatta cattcatgtc    1020
tgtagaacac cttgcgacga ttgcaaacat tggtgtgcat gccgaaggcg cgctacactc    1080
atcgcccctc cctcattgga gcttggcaaa cttaattgta gtagacggta gggaagtctt    1140
tatgctataa ggccttaaag gaccagcgca ccagaacaac aaccgtgacc attaaagaaa    1200
agcaaaaaga aagaaaagc atagatggaa aagattcaac atgtagacat ataacacagc    1260
aaaactaagg ccgaatccaa gtatatccac taaactcaaa cactgactga atcccgcgag    1320
attcaccgac aatgccctcc gacaatgtta gatgcatcat gggatagggg acttggcagg    1380
gtgaacctta ttctgtcttc agatagcaga tgtcgcctca ccttcctaag cagcacacaa    1440
acactaaata aaacttgaaa acacttaaa atgaagtagg agcactctca ctggcaagag    1500
ccacgatcca ttatgcctcc atggccctaa agcggaggaa agatcgatgg cagcatcggg    1560
gggaggcgag gaagccctcg tttcctggga gttcgcttgt ggagcactaa tactatcttg    1620
atactagcta ccatagactg cagtggtaag atgtacatac tgaagtgatt ttttttttctg    1680 tcggcgtgaa tgtacttact accaggttgc caggcaaaag ctttgcgagc aatcaacatg    1740
tttggctgta caacgctcag aacgcaaaca ccagagtttt cccccgcgcg ctcttagcaa    1800
```

-continued

```
aggtatatct cttctactta tctcatatta tgtgtgtata gcaatgatgc gggtcgggtt    1860
ttcaaccccc ttacataaga aaacatcgtt tggtctttaa ctaataataa tactccaaaa    1920
cgtgcatgat gtcttcctac accatccgat ggtcaaatca gaccgcttct attcaggtca    1980
gcacattact tcctactata gatagataga tagacgcaca catatacaca tctctgatct    2040
caaaccgttc acatatttcc agacaatcgt ttgcattccc ttcatgggcg gtgtgctgga    2100
gctcggaacg tcggatcagg tcggtgcaca tgagtttcaa tttatgttct cagtaactct    2160
cagcatgttc ttccgacttg ccgacgggtt caacggtaac cttttaatat taggggtagc    2220
tattttgttt gccaatacat gctagctatt tttgtatgtg ttgtcccagt ctaccattct    2280 gcccctttg catttatgcg ttattccttt ttagtacatt aatttacact agtcttccac    2340
tgcgttttcc tactactatg tattttatat tatatttgtg attatcttta gagcaagtac    2400
aatagagtga tgtaggcggg ctacaagaga tggcacatca cttttatgcc tagttgaagg    2460
agagaggaga ggagagaaga gaagcgggtt acaaacttac agcaaaagtg accccaccta    2520
tatataaggc ttttaatcag tagtgtctgc ctcacacaca cagatactct aggttcctct    2580
taacacacca tctccctctg ttcgactgtc cctacacaca gtctctatcc atctctctct    2640
agatgtatgc ccccatagga gggtgactgc cgtcgacgtg gatagtgatt gggattgaga    2700
tctcatggca agggggacca gatatttaca ccactggcga gggatccact agttgtattt    2760
gagagttgag actatcgatg acggatgcgt tcaatgggtt tttggcagtg cgtgaacttg    2820
cttttctctc tttcccgtcc cccgtataac tctattctga gttgtattat tgttatcagt    2880
aacgaaaagg gtatacccga ttaaaagaaa aggctgtatt tgaggtactc atgtatatat    2940
gttttgtata gtgggaaaaa tgataatata tgtgtagcgg ccgcacgcat cttgaggaca    3000
gattccttac cagtacgtac caccatagcg gtaaaaatgc ctttgcgagt agctaccaca    3060
ttaacacttg gccaagtttt tcctttcgtc gtcgtccgtc cacgtaaagc aaatgctatt    3120
gacgattgac aaagtgtatc ctatatttcc aaggttttgg aggaccccgg catggtgaag    3180
cggatcagca cgtctttctg ggagctgcac ttgccgtcat ccttggagtc gaaggatgcg    3240
agctccagca catcagcgaa cgataccagg gaggccaccg acatcatctt gttcgaggac    3300
ttcgaccaca acgacacagt tgagggggtc acctctgagc aaagggaggt ccagtgcctg    3360
tccaacgtca atctggagcg cctcacaaag cagatggacg agttccacag ccttctcggt    3420
ggactggacg tgcatcctct cgaagacaga tggatcatgg acgagccctt tgagtttacg    3480
ttttccccgg aactggcgtc ggctatggat atgccgagca ccgacgatgt catcgtcact    3540
ttaagtaggt ctgaaggctc tcgtccatcc tgcttcacgg cgtggaaggg atcatccgag    3600
ttgaaatacg tgcctggcca ggtcgttggg gagtcacaga agttgctgac taaagttgtg    3660
gctggtggtg catgggcgag caattatggc ggtcgcacca cggtgagagc tcaggaaatt    3720
aacaacaaca cccatgtcat gacagagaga agacgccggg agaaactcaa cgagatgttc    3780
ctggttctca agtcactagt cccgtccatt cacaaggtag taatatgtag agtccattta    3840
ccatcagcaa attgcacacg ttgttttttca tagttttttt actgctggat tgcaggtgga    3900
caaagcatcc atcctcacag aaacgatagg ttatcttaga gaactgaagc aacgggtaga    3960
tcagctagaa tccagccggt caccgtcttg ttggatatta tga                      4003
```

<210> SEQ ID NO 11
<211> LENGTH: 1344
<212> TYPE: DNA
<213> ORGANISM: Elytrigia elongata

<400> SEQUENCE: 11

```
atggcgctat cagctcctcc cagtcaggaa cagccgtcgg ggaagcaatt cggctaccag      60
ctcgctgctg ctgtgaggag catcaactgg acgtatgcca tattttggtc catttccgcc     120
agcccgcgcc caggccactc ctcagttctg gcgtggaagg atgggttcta caacggcgag     180
ataaagacaa gaaagattac cggctcgacc actacggagc ttacagcgga cgagcgcgtc     240
atgcacagaa gcaagcaact gagggagctc tacgaatcgc tcttgcccgg caactccaac     300
aatcgggcaa ggcgacctgc cgcctcactg tcaccggagg atctagggga cggcgagtgg     360
tattacacca taagcatgac ttacaccttc caccctaatc aagggttgcc aggcaaaagc     420
tttgcgagca atcaacatgt ttggctgtac aacgctcaga acgcaaacac cagagttttc     480
ccccgcgcgc tcttagcaaa gaccgcttct attcagacaa tcgtttgcat tcccttcatg     540
ggcggtgtgc tggagctcgg aacgtcggat caggttttgg aggaccccgg catggtgaag     600
cggatcagca cgtctttctg ggagctgcac ttgccgtcat ccttggagtc gaaggatgcg     660
agctccagca catcagcgaa cgataccagg gaggccaccg acatcatctt gttcgaggac     720
ttcgaccaca cgacacagt tgaggggtc acctctgagc aaagggaggt ccagtgcctg     780
tccaacgtca atctggagcg cctcacaaag cagatggacg agttccacag ccttctcggt     840
ggactggacg tgcatcctct cgaagacaga tggatcatgg acgagccctt tgagtttacg     900
ttttccccgg aactggcgtc ggctatggat atgccgagca ccgacgatgt catcgtcact     960
ttaagtaggt ctgaaggctc tcgtccatcc tgcttcacgg cgtggaaggg atcatccgag    1020
ttgaaatacg tgcctggcca ggtcgttggg gagtcacaga agttgctgac taaagttgtg    1080
gctggtggtg catgggcgag caattatggc ggtcgcacca cggtgagagc tcaggaaatt    1140
aacaacaaca cccatgtcat gacagagaga agacgccggg agaaactcaa cgagatgttc    1200
ctggttctca gtcactagt cccgtccatt cacaaggtgg acaaagcatc catcctcaca    1260
gaaacgatag gttatcttag agaactgaag caacgggtag atcagctaga atccagccgg    1320
tcaccgtctt gttggatatt atga                                           1344
```

<210> SEQ ID NO 12
<211> LENGTH: 447
<212> TYPE: PRT
<213> ORGANISM: Elytrigia elongata

<400> SEQUENCE: 12

```
Met Ala Leu Ser Ala Pro Pro Ser Gln Glu Gln Pro Ser Gly Lys Gln
1               5                   10                  15

Phe Gly Tyr Gln Leu Ala Ala Ala Val Arg Ser Ile Asn Trp Thr Tyr
            20                  25                  30

Ala Ile Phe Trp Ser Ile Ser Ala Ser Pro Arg Pro Gly His Ser Ser
        35                  40                  45

Val Leu Ala Trp Lys Asp Gly Phe Tyr Asn Gly Glu Ile Lys Thr Arg
    50                  55                  60

Lys Ile Thr Gly Ser Thr Thr Thr Glu Leu Thr Ala Asp Glu Arg Val
65                  70                  75                  80

Met His Arg Ser Lys Gln Leu Arg Glu Leu Tyr Glu Ser Leu Leu Pro
                85                  90                  95

Gly Asn Ser Asn Asn Arg Ala Arg Arg Pro Ala Ala Ser Leu Ser Pro
            100                 105                 110

Glu Asp Leu Gly Asp Gly Glu Trp Tyr Tyr Thr Ile Ser Met Thr Tyr
```

```
              115                 120                 125
Thr Phe His Pro Asn Gln Gly Leu Pro Gly Lys Ser Phe Ala Ser Asn
        130                 135                 140

Gln His Val Trp Leu Tyr Asn Ala Gln Asn Ala Asn Thr Arg Val Phe
145                 150                 155                 160

Pro Arg Ala Leu Leu Ala Lys Thr Ala Ser Ile Gln Thr Ile Val Cys
                165                 170                 175

Ile Pro Phe Met Gly Gly Val Leu Glu Leu Gly Thr Ser Asp Gln Val
            180                 185                 190

Leu Glu Asp Pro Gly Met Val Lys Arg Ile Ser Thr Ser Phe Trp Glu
        195                 200                 205

Leu His Leu Pro Ser Ser Leu Glu Ser Lys Asp Ala Ser Ser Ser Thr
    210                 215                 220

Ser Ala Asn Asp Thr Arg Glu Ala Thr Asp Ile Ile Leu Phe Glu Asp
225                 230                 235                 240

Phe Asp His Asn Asp Thr Val Glu Gly Val Thr Ser Glu Gln Arg Glu
                245                 250                 255

Val Gln Cys Leu Ser Asn Val Asn Leu Glu Arg Leu Thr Lys Gln Met
            260                 265                 270

Asp Glu Phe His Ser Leu Leu Gly Gly Leu Asp Val His Pro Leu Glu
        275                 280                 285

Asp Arg Trp Ile Met Asp Glu Pro Phe Glu Phe Thr Phe Ser Pro Glu
290                 295                 300

Leu Ala Ser Ala Met Asp Met Pro Ser Thr Asp Asp Val Ile Val Thr
305                 310                 315                 320

Leu Ser Arg Ser Glu Gly Ser Arg Pro Ser Cys Phe Thr Ala Trp Lys
                325                 330                 335

Gly Ser Ser Glu Leu Lys Tyr Val Pro Gly Gln Val Val Gly Glu Ser
            340                 345                 350

Gln Lys Leu Leu Thr Lys Val Val Ala Gly Gly Ala Trp Ala Ser Asn
        355                 360                 365

Tyr Gly Gly Arg Thr Thr Val Arg Ala Gln Glu Ile Asn Asn Asn Thr
370                 375                 380

His Val Met Thr Glu Arg Arg Arg Glu Lys Leu Asn Glu Met Phe
385                 390                 395                 400

Leu Val Leu Lys Ser Leu Val Pro Ser Ile His Lys Val Asp Lys Ala
                405                 410                 415

Ser Ile Leu Thr Glu Thr Ile Gly Tyr Leu Arg Glu Leu Lys Gln Arg
            420                 425                 430

Val Asp Gln Leu Glu Ser Ser Arg Ser Pro Ser Cys Trp Ile Leu
        435                 440                 445

<210> SEQ ID NO 13
<211> LENGTH: 1952
<212> TYPE: DNA
<213> ORGANISM: Elytrigia elongata

<400> SEQUENCE: 13
ctccgctatg tctatggcac tatggatctt ggcgtcacgc ttcacgcctc cgccgacacc      60
gccctcaccg cctactccga tgcagactgg gcgggctacc ctgacactca tcgctccacc     120
tcgggctatt gtgtctacct tggaccctca cttatttcgt ggtcgtccaa gcggcagcct     180
acggtctctc gttccagtgc tgaggctgag atcgtgcggt ggccaacgc cgtcgccgag     240 tgttcgtggc ttcgccagct gcttcaggag ctttcctgcc ctgttgactg tgccacggtg     300
```

```
gtctactgcg acaacgtctc ggcggtctac ctctccgcta acccggtgca tcatcgacgg      360
accaagcata ttgagttgga tattcatttt gttcggaaac aggtggccct tggtcatatt      420
cgtgttttac accaggggcg gaactgggcc tggggcaact ggggctatag ccccaggcat      480
ggcccatcta gtaggctacc cagcaggaat tttcccatat attagtacac ttgtagaggc      540
ccagccccag gcctcagccc acagagctct ccagtttgga cgatcgctcc aaagaatcac      600
cagcagccac gatgcaagag cgctccgatc ctcacgcttc gtctcggtag atcgaccgaa      660
aagtctcacg ctgcgccgcc aactctctcg actgctcgac tccagcagac gctcgcccag      720
gcggccggcg ctcggaaccg cggatctatc gcgccgtttg aataaagcaa tctccatgcc      780
tgatctcctg tgatccacac ccgattgaaa aggtaatgct aaatacctag gtttgtcgta      840
tcatctaata tttccccccta gttccttttt atcagctgaa atcaatgaat tggtgatgtt      900
aaattgtatt gctttagtca atttttattcc atcgttcttt gttaacaggg gaaaaataga      960
aatccaagat gaagtggacc cggacagttt tcgtgatca tggtataata ttttcttgct      1020
tcccaaaatt tcatatgaac aataacttgt ctatgtctag ttcttgattt taaatactca      1080
actttatgtt tacagctccg ggtcctagct actattgctt gtgaagaaac gatggcctca      1140
agtgagacaa gccttcatta atttggtacg actgtttgta atgatgcact ttgttatatt      1200
gatgagatat ttattaaatt tgctcttatg gtaataagta attcatattc tattcttaat      1260
ctgaatgtgt ggtgtacttc taacatgcat tggtacgtag agtatttggc attttatttc      1320
ctttaggttg tgatatttgg cgttatttgt agtggtttag ctttagtcct aggcttcgag      1380
aaatcctggc tccgcctctg ttttacacgt tcctacttttt caacaatttg cagatattat      1440
gaccaaaggc ttgcctacgg cgtcatttaa ggagttccgg tccagtcttt gcgtcagccg      1500
cggtgccgct tcgactgcgg ggggtgttga gtacatgtgt tatgtgtata ttgtgtattg      1560
ggtccgtctc ctagttcttt gtatagttga ggtctatggc ccaccgttgt acatcatata      1620
tacgtgccta tgcacgagag caatacatca tgcaatcata gtctcataca ctagcgatct      1680
gaagctttac accaggttat aggttttctt cctcgacttt ggacggatat catcatcggt      1740
gccgccggtg agatgtatag gcggcggaac ggcggtgctg aacgtccgtg ttcattgcac      1800
agatggatcc tttgctagcc gtttggtgta cctaactcgg acttaggtgt tgcttgcggt      1860
gaccacatgg tgtattaata aagcacaacg gccttctgcc cacggatcaa acacagtaca      1920
cacgggcagt tgggaaaaag ataacgggga gg                                   1952

<210> SEQ ID NO 14
<211> LENGTH: 2013
<212> TYPE: DNA
<213> ORGANISM: Elytrigia elongata

<400> SEQUENCE: 14
ggtcaccaaa acacataact cataatacaa atcatcatcg aacgctaagc gtgtggaccc       60
tacgggttcg agaactatgt agacatgacc gagacagatc tccggtcaat aaccaatagc      120
ggaacctgga tgctcatatt ggctcctaca tattctacga agatctttat cggtcaagcc      180
gcataacaac atacgtcatt ccctttgtca tcggtatgtt acttgcccga gattcgatcg      240
tcggtgtcat cataccctagt tcaatctcgt taccggcaag tctctttact cgttccgtaa      300
tgcatcatcc cgcaactaac tcattagtca cattgcttgc aaggcttata gtgatgtgca      360
ttaccgagag ggcccagaga tacctctccg atacacggag tgacaaatcc taatctcgat      420
```

| | |
|---|---:|
| ctatgccaac tcaacaaaca ccatcggaga cacctgtaga gcatctttat aatcacccag | 480 |
| ttacgttgtg atgtttgata gcacacaaag tgttcctttg gtattcggga gttgcataat | 540 |
| ctcatagtca gaggaatatg tataagtcat gaagaaagca atagcaataa aactaaacga | 600 |
| tcataatgct aagctaatgg atgggtcttg tccatcacat cattctctaa tgatgtgatc | 660 |
| ccgttcttca aatgacaaca catgtctatg gtcaggaaac ttaaccatct ttgattaacg | 720 |
| agctagttaa gtagaggcat actagggcca ctctatttgt ctatgtattg acacatgtac | 780 |
| taagtttccg gttaatacaa ttctagcatg aataataaac atttatcatg atataaggaa | 840 |
| atataaataa caactttatt attgtctcta gggcatattt ccttcagtat gaaggccgac | 900 |
| tgatctgggt gggtgatgcg gttggccaaa ggagtcaccc tattgacgta cccctttgcc | 960 |
| aagatgcggg agatcacatt gatcacggta atcaccctgt tgcttttgta aagaatggag | 1020 |
| ttatgagaat aggtgaaata tgctttgtgg gacgaaattg actacgcatt ttgtgtataa | 1080 |
| tcagggttta gaagtccatt gtgtgtgcat gtttgatacg agatatgttg ctcgtatgaa | 1140 |
| aagaactata tctgcaaagc tatatttagt tcaaattaag atttgagcta cattattgca | 1200 |
| ctcgttcatt ttattgagat aattatggcc taactaggat gactgagaat tttttctatg | 1260 |
| attatacgtg caacgcacgt gcatacttac tagtaaaaat gaaaatctaa cgcaataagt | 1320 |
| gaaaaacggg gcggcatagt gcaacacttt gctctacagg ccaacatcc tcgttgaaca | 1380 |
| tgcactacaa atactccctc cgtaaagaaa tataagagcg ttagcgatcc tcttatattt | 1440 |
| ttattacgga gggagtacta gctaggaata tcgcaaagca gtcgtcgtct ctggctccgg | 1500 |
| tcaaaaccag agcaagactt tcgtctcgtc tttctctcgg gcgcccactg cacggcagga | 1560 |
| gcgtatctgg gactgggaca gggaggccaa ccacgcgtag tagtagcgga gcaccagctc | 1620 |
| atggcccgca atgcatgcaa gatgtaaccc acagtcccgg tcctgcgccc gacaggctac | 1680 |
| gcctggagga gtcgccactg ccatctgtcc acgccaggtg tgagagatcg gagtgggcct | 1740 |
| agcgatctga agttttacac caggttttct tcctcgactt tggacggata tcatcatcgg | 1800 |
| tgccgccagt gagatgtata ggcggcggaa cggcggtgct gaacgtccgt gttcattgca | 1860 |
| cagatggatc ctttgctagc cgtttggtgt acctaactcg gacttaggtg ttgcttgcgg | 1920 |
| tgaccacatg gtgtattaat aaagcacaac ggccttctgc ccacggatca aacacagtac | 1980 |
| acacgggcag ttgggaaaat gataatgggg agg | 2013 |

<210> SEQ ID NO 15
<211> LENGTH: 2084
<212> TYPE: DNA
<213> ORGANISM: Elytrigia elongata

<400> SEQUENCE: 15

| | |
|---|---:|
| tttcttaggg cattatgatg atgacttggc atcactagtg cggagttact gtagcatgat | 60 |
| tctcggggtg tcacaacagt acatcctaga gatcttggat cgcgccaata tgaccaactg | 120 |
| taaccccact gctactcctg tcgacaccaa atccaaacta tccgctactg acagtccacc | 180 |
| agttcccgat cctactctat gtcgtagcat tgctggagcc ttccagtgcc tcacccgcac | 240 |
| tcaccccgat atctcctatg cggtacagca ggcctgccta tttatgcacg atcctcgcgc | 300 |
| ccccaccttc agttcgtcaa aaggatctta cgctatctca aggccacatc acattatgga | 360 |
| ctgcagctta ccacttctcc tggacatgat ctcgtggctt attccgacgc agattgggcc | 420 |
| ggctgtcccg ctacactgaa gtccacctct ggttctgtg tgttccttgg ccccaacttg | 480 |
| gtatcttggt cctccaaacg ccaacacacc gtctcttgat cgagcgccga agctgagtat | 540 |

```
agggcggttg caaattgcgt cgctgaatcc tgctggcttc gccagcttct acaggagcta      600
catcaacctt cgtctagcgc cacaatcgtt tacactgaca acatcagtgg gacgtacctc      660
tcctccaacc ccgtctagca ccaacgcacc aagcacgtca agatcgactt gcattttgtc      720
cgagatcggg tggcacttgg agaggctcgg atcctgcacg tttcgtccaa ctcccaattt      780
gcggacgtgt tcaccaaggg cctgcctaca tccatcttcc atgagtcttg ttccagtctg      840
aacatccacc gtgtggagct ccgactgcgg ggtgctgtta aagtgtgttg taatattgta      900
catagacttg tcacgttgag gcctgcatgc ccatctgttg aaactacctc cacctctctg      960
ggatcacgat cccccttctc aattttttt ttgaacacag tacagacgca agcactcata     1020
tacacgcgca tacactcacc cctatgaacg cacacacgca caccctaccc ctatgagcac     1080
ccccgaaaga ctgagccagc atatcatctt gaaatttacg aaatcaccgt agtcacctcg     1140
tcgtcgacgg gaacgtctcc tcccactgaa tgcacatcgc cggaaatcct gaaatgaatc     1200
caggaataaa tgcgagcacc aggatttgaa ccctggtggg ttggggatac cacagtccct     1260
ctaaccatcc aaccacaggt tggttcgcat ccccttctc agttgatggc ctgcgtgcct      1320
acttcttcgg cagtagttgc agctctcaat atatgtactc tgactcccct aaaatatata     1380
tatatatact ctgaccactg gttgtaatgt aacacgaaca cacagtgagg aattccaaac     1440
cataacttgg ttgtggggtg accattccac agcgttttat gcaacgtggc ggcagactag     1500
gttattcaca caaaaaagat ccatgcaagt ttccacgtgc tgctgcttcc aacgttgaag     1560
tgttttctgt gtcgtgcgtc gatcgtattt ggatcttctc agcaacgata gcggcgagat     1620
ttcgttgtat ctatgtcttc agagcggttc gagtagattt tttccttcat ttttcggact     1680
gaagaaaaag aggaaatgct accttccatc gttcgtactg tgtagttgtt ggtgcaacag     1740
cccgcgcatt tgcataaggt gccttgtata tatgtggaaa cgttcagttg ctacgtacct     1800
cttcgtggtc tgcacacgca tacagtctgc acactgatac cttaaagtaa gctttaattt     1860
tgcttcagtt tacttctcca gttcttggct agctgaatct cgacttctag tttggtcgga     1920
atttatataa cttcctgcg tgtacagtac acagcgtatg taccatgcat ataactttat      1980
ataccttct tgatttcttt tgctgcttgt ttcctcgacc tagcgtctca ccttgtgagt      2040
tgtgcatgcg ggaaatagct actcagcggt gtggtaatcg atca                      2084
```

<210> SEQ ID NO 16
<211> LENGTH: 2022
<212> TYPE: DNA
<213> ORGANISM: Elytrigia elongata

<400> SEQUENCE: 16

```
caacccaagc atctcttttc tgtcaccacc accatggaca tttctcccat accttctacc       60
tataaatctg ccttaaaaaa tccccattgg tacaatgtaa tgcttgaaga atttaatgct      120
ttgtagaatg atacatggtg tttggttcct cgacctgcag gtgtcaacat ggtcaccgag      180
aaatggatct ttaggcacaa atttcattcg gacggctccc tagctcgcta caaggcccat      240
tgggttctcc gtggattcac tcagcaggag ggcgtcgact acactgagat attttgtccg      300
gttataaaac cggccacagt tcgggtgctt ctcagcctcg ccaccactca ttcttggccc      360
attcatcaaa tggatctcaa gaacgccttc ctccatggca ctctcggtga aaccgtttac      420
tgcaatcaac cggctgggtt cattgattca tctcaccgca cccatgtttg tcttctcaag      480
aaatctttat attggttaaa acaggctcct cgcacatggt ttatctgttt ccaggccttc      540
```

```
atcctttcct tgggatttgt tgcttctaag tgcgactctt cactgttcat tcttcatcgt    600
ggctcggcca ttgcctatct tctcctttat gttgatgata ttatcctcac tgttaacacc    660
accgccacct tacactccat catcttctcg ctcaagcccg agttatctat gtttgacttc    720
ggtgacatac atcatttcct tggtgttaat gttacccgtt ccccacgtgg cctcttttta    780
tctcaagaat agtacatctt agagatcttg gattgcgcca atatgaccaa ctgtaacccc    840
attgctactc ctgtcaacac caaatccaaa ctatccgcta ctgacagtcc accagttccc    900
gatcctactc tataccgtag cattactgga gccctccagt acctcaccct cactcgcccc    960
gatatctcct atgcgttaca gcaggcctgc ctatttatgc acgatcctag cgcctcccac   1020
cttcagtttg tcaaaaggat cttacgctat ctcaaggcca catcagatta tggactgcag   1080
cttaccactt ctcctggaca tgatctcatg gcttattccg atgcagattg gccggctgt    1140 cccgctacac tgaagtccac ctccggtttc tgtgtgttcc ttgaacccaa cttggtctct   1200
tggtcctccg agcggcaaca cactgtctct tgatcgagcg ccgaagctga gtataggggg   1260
cagttgcaaa ttgcgtcgct gaatcctgct ggcttcgcca gcttctacag gagctacatc   1320
aaccttcgtc tagtgtcacc attgtttcct gtgacaacat cagggcgacg tacctctcct   1380
ccaaccccgt ccagcaccaa cgcaccattc cacaacgttt tatgcaacgt ggcggcagac   1440
tagtttattc acacaaaaaa gatccatgca agtttccacg tgctgctgct tccaacgttg   1500
aagcgtttct tgtgtcgtac gtcgatcgta tttggatctt ctcagaaacg atagcggcga   1560
catgtcgttg tatctatgtc ttcagagcgg ttcgagtaga ttttttcctt cattttcgg    1620 actgaaaaaa agaggaaatg ctaccttcca tcgctggtac tatgtagttg ttggtgcaac   1680
agcccgcgca tttgcataag gtgccttgta tatatgtgga aacgttcggt tgctacgcgc   1740
gtacctcttc gtggtctgca cacggatacc ttaagtaagc tttaattttg cttcagttgg   1800
aagccagcca gtttacttcc cccgttcttg gctagctgaa tctcgacttc tagtttggtc   1860
ggaatttata taactttccg gcgtgtacac agcgtacgaa ccatgcatat aactttatat   1920
acctttctcg atttcttttg ctgcttgttt gctcgaccta gcgtctcacc ttgtgagttg   1980
tgcatgcggg aaatagctac tcagcagtgt ggtaatcgat ca                      2022
```

<210> SEQ ID NO 17
<211> LENGTH: 441
<212> TYPE: DNA
<213> ORGANISM: Elytrigia elongata

<400> SEQUENCE: 17

```
gtacccagta taaccgtaca tgcacccaac caactatata gtgtaaggaa taaaacgacg     60
tcattagcac tggagggctg ccacgtcggc cggcggatct ttggctcgcg agtcgttgga    120
tgtggcacaa ttcagcagct caacgtctcc ctctacttcg caacagagtt tttgttttt     180 atttgcgctg gtaaaggagt tttattccat atgcataggg ttacaatcaa gaggcaggag    240
atcctccaca cacggcggac ctcgaccaag ccatacagca gtagtgctct ctgtacgact    300
atacagggcc aaacgatctg ctaccctatt ctgcagacga ctaattttca tgggaataaa    360
aactctatct accataagat gacgaatctc agcaactata tgtccatagg ctgatctggt    420
taaactgtca ccagacaaag c                                              441
```

<210> SEQ ID NO 18
<211> LENGTH: 163
<212> TYPE: DNA
<213> ORGANISM: Elytrigia elongata

<400> SEQUENCE: 18

| | | | | | |
|---|---|---|---|---|---|
| ctctcacaca | tcatcgagtt | aagtacccag | tataaccgta | catgcaccca | accaactata | 60 |
| taatgtaagg | aataaaacga | cgtcattagc | actgggggc | tgccgcgtcg | gcgatgtgac | 120 |
| acaattcagc | agctcaacgt | ctccctctac | ttcgcaacag | aga | | 163 |

<210> SEQ ID NO 19
<211> LENGTH: 618
<212> TYPE: DNA
<213> ORGANISM: Elytrigia elongata

<400> SEQUENCE: 19

| | | | | | |
|---|---|---|---|---|---|
| gcaagacttt | tttgacacta | gtgtattgtt | aaaaacgtct | tatattacga | gacgaaggga | 60 |
| gtacttaaca | actcaatcta | caaaaaatca | tgagttgggc | tctatagtct | gcttcgccca | 120 |
| acaaccaggt | cggactagtg | tgaattactg | tacaccaaaa | aaattctgaa | ataattactg | 180 |
| aacacgtcat | gacgtgtcta | cttccctcca | aaagtatttc | agatctacat | tccgcctgtc | 240 |
| aattaagcac | gaaatttgaa | gccgattgtg | ctgcccggcc | ctactcacca | ctacagaaat | 300 |
| gcctagctag | cggtggcggc | actaccgttc | ggattctttc | cagcttcctg | aaatagccag | 360 |
| cttcccgcga | tgccagccgc | agccagcttc | tgacgggagt | agcgattcgt | tcggcagcag | 420 |
| agagtagctc | tagacaccgt | acgaacttga | atagcccag | gaaggaagcc | ggcgtgaggg | 480 |
| agggagctag | gaggagtgag | ctctctggcg | tggatacggc | ggcaagctcg | atggagcagg | 540 |
| tcgaccaggt | gccgacggcg | agcaacagag | gaagttgagg | cagggtcggg | cgtccgggtg | 600 |
| cgctgaggat | gggccatg | | | | | 618 |

<210> SEQ ID NO 20
<211> LENGTH: 741
<212> TYPE: DNA
<213> ORGANISM: Elytrigia elongata

<400> SEQUENCE: 20

| | | | | | |
|---|---|---|---|---|---|
| tcttaaagac | taaattgtag | ccattatgtt | ttaataataa | agataaagct | taagtgcaaa | 60 |
| atatctgatg | tgctacagtg | acaaacagta | ggtcggtgct | acagtgccca | cctactctga | 120 |
| tgagctgccc | tgatcagggg | tagctcatca | gccaactcat | ggtgtgggcc | ccttggtgca | 180 |
| cagtgctatt | catatgaaga | taaggagaa | gagaatagag | cagctaagtg | agttagttct | 240 |
| ggctgctgct | gctctgagcc | tattcctctc | tcttccccac | acaaaacact | aaaggaaagg | 300 |
| gctactgatc | aagcctgcac | tggagcactg | gaaggacct | ctcacagcca | tcagattgag | 360 |
| ttcttggtgg | tgttgagcta | agaaaggag | atggcaggac | ctgcaggtca | aggtatgttt | 420 |
| atctcctaac | caagtttgtg | gctcaaactt | gtgctaaatg | atcctggagc | aatccaacaa | 480 |
| tggtatcaga | gcccaatagc | atcatgtttg | agccctataa | gtaataaatc | agacttggtc | 540 |
| tgttgcaatt | aagttaaagt | atcaagctgc | tcttcctaaa | gatcaaggtt | tgatcttatt | 600 |
| tgagcccta | tgagcaatag | atcatgtctg | atctgttata | tataagttaa | gttttgatt | 660 |
| aagctcatgt | tgttcttcct | atttaagtca | aggaagtcct | cgaacaagat | gatgtcgcct | 720 |
| atcttttcta | ctactacttt | g | | | | 741 |

BLUE-GRAINED GENES IN WHEAT AND APPLICATION THEREOF

TECHNICAL FIELD

The disclosure relates to the fields of plant molecular biology, biochemistry, genetics and plant breeding, and particularly relates to genes for controlling a blue-grained wheat trait. The disclosure provides nucleic acid molecules and plant recombinant vectors of four genes controlling blue-grained wheat trait, and use methods of these genes or vectors.

BACKGROUND

Grains of common wheat have two colors naturally: a white grain or a red grain, in addition, a very few cultivars are blue-grained or purple-grained. The blue grain or purple grain wheat can be used as an important genetic marker applied to genetic breeding in wheat, especially in China, the blue-grained wheat has been successfully used, for example, a '4E-ms system of producing hybrid wheat' has been established to maintain genetic male sterility in wheat by use of the blue grain trait. (Zhou et at, 2006).

The endosperm of the wheat grain is covered by three layers of tissues from outside to inside, respectively including: the pericarp, the epidermis and the aleurone layer, the grain color of the wheat is determined by different anthocyanin accumulated in the different tissues. The color of the purple grain wheat is derived from the purple anthocyanin in the pericarp on the outermost layer, which develops from maternal tissues, so the color inheritance of purple grain wheat follows a maternal inheritance pattern. But the color of blue grain wheat is derived from the blue anthocyanin on the aleurone layer, and the blue grain is mainly generated by far-source hybridization between the common wheat and other species, and there are two sources of the blue-grained wheat: *Thinopyrum ponticum* and *Triticum monococcum*. In the 1960s to 1980s, many scientists at home and abroad, such as Knott, Sharman, and Li Zhensheng, obtained the blue-grained wheat from the progenies of the hybrids between *Thinopyrum ponticum* and the common wheat, and proved that the 4E (also named as 4Ag) chromosome of *Thinopyrum ponticum* carries blue-grained genes. By genetic analysis, Li et al demonstrated that the inheritance of the blue grain trait is stable and independent, and exhibited a dosage effect, and the blue grain trait seemed to be controlled by a pair of genetic loci (Li et al, 1982). Through GISH and FISH analysis of a set of blue-grained translocation lines, the blue-grained gene is further mapped to the 0.71-0.80 region (distance measured from the centromere) of the long arm of 4Ag chromosome (Zheng et al, 2006). In 1990, Keppenne named the blue grain gene from *Thinopyrum ponticum* as Ba (Blue aleurone) gene, and there were also other scientists considering that the blue grain trait is controlled by two complementary genes. In 1982, Joppa et al proved that the Blaukorn strain received the blue grain color through chromosomal substitutions of 4A and 4B chromosomes of common wheat with 4A$^m$ chromosomes of diploid wheat *Triticum monococcum*, and the 4A$^m$ chromosome from *Triticum monococcum* is not homologous with the 4A chromosome in tetraploid or hexaploid wheat. In 1989, Kuspiral et al named the blue aleurone layer gene from the *Triticum monococcum* as Ba2, and the Ba2 gene is mapped to the long arm of the 4A$^m$ chromosome near the centromere (Dubcovsky et al, 1996).

So far, the genes controlling red grain and purple grain in wheat has been cloned already, and it is not reported about the blue-grained trait. In 2005, Himi reported that 3 red grain color genes located in 3AL, 3BL and 3DL chromosomes, respectively, encode highly homologous Myb family transcription factors. (Himi et al, 2005). Genetic analysis of the purple grain wheat showed that the purple grain trait is controlled byPp-1 (purple pericarp) site located in the short arm of Chr.7B and Pp3 site located in 2AL chromosome, herein Pp-1 encodes a Myb family transcription factor and Pp3 encodes a Myc family transcription factor containing bHLH (basic helix-loop-helix) motif (Khlestkina et al, 2013; Shoeva et al, 2014).

Anthocyanins for determining the wheat grain color are water-soluble secondary metabolite (a flavonoid compound), which are ubiquitously distributed in root, stem, leaf, flower, fruit and seed of higher plants. Plant anthocyanin biosynthetic pathway belongs to a branch of flavonoid biosynthetic pathway, the main enzyme involved in the anthocyanin pathway includes chalcone synthase (CHS), chalcone isomerase (CHI), flavanone-3-hydroxylase (F3H), dihydroflavonol-4-reductase (DFR) and so on (Gong jia and the like, 2011), which are structural genes of the anthocyanin pathway. But the regulation of the anthocyanin biosynthetic pathway is performed by three types of the transcription factors: MYB, bHLH and WD40. Most anthocyanin biosynthesis is directly activated by a protein complex composed of the three types of transcription factors, and a small number of the anthocyanin biosynthesis may be activated by one single regulating factor only.

The blue-grained wheat trait is an ideal morphological feature for wheat selected markers and cytogenetic research, and it is also an important basic material in wheat chromosome engineering research. The disclosure obtains four genes controlling blue-grained trait in wheat by differential expression analysis between blue-grained and white-grained wheat: two MYB family transcription factors and two bHLH family transcription factors. The disclosure is helpful to research the aleurone layer pigment biosynthetic pathway of blue-grained wheat, and may be used as a selected marker in plant transformation system, and the expression of these genes could increase the content of anthocyanin in plants, so does the nutritional value of the plants, so the nutritional value of the plant is improved.

SUMMARY

All references mentioned in this text are incorporated into this text by reference.

Unless otherwise specified, all technical and scientific terms used in the text have the same meanings as that understood by those of ordinary skill in the art of the disclosure. Unless otherwise specified, technologies used or mentioned in the text are standard technologies publicly known by those of ordinary skill in the art. Materials, methods and examples are only used for explaining, and are not Intended to limit.

The disclosure provides blue-grained genes which regulate the anthocyanin biosynthesis pathway, the blue-grained genes are respectively named as ThMYB1, ThMYB2, ThR1 and ThR2, and the expression of the blue-grained genes may change a tissue or an organ into blue. Herein a genome nucleotide sequence of the ThMYB1 gene from an initiation codon to a termination codon is as shown in SEQ ID NO: 1, the nucleotide sequence of a coding sequence (CDS) thereof is as shown in SEQ ID NO: 2, and an amino acid sequence coded by the CDS thereof is as shown in SEQ ID NO: 3.

Herein the genome nucleotide sequence of the ThMYB2 gene from the initiation codon to the termination codon is as shown in SEQ ID NO: 4, the nucleotide sequence of the coding sequence (CDS) thereof is as shown in SEQ ID NO: 5, and the amino acid sequence coded by the CDS thereof is as shown in SEQ ID NO: 6. Herein the genome nucleotide sequence of the ThR1 gene from the initiation codon to the termination codon is as shown in SEQ ID NO: 7, the nucleotide sequence of the coding sequence (CDS) thereof is as shown in SEQ ID NO: 8, and the amino acid sequence coded by the CDS thereof is as shown in SEQ ID NO: 9. Herein the genome nucleotide sequence of the ThR2 gene from the initiation codon to the termination codon is as shown in SEQ ID NO: 10, the nucleotide sequence of the coding sequence (CDS) thereof is as shown in SEQ ID NO: 11, and the amino acid sequence coded by the CDS thereof is as shown in SEQ ID NO: 12.

It is to be noted by those skilled in the art that the blue-grained gene of the disclosure further includes a nucleotide or protein sequence which is highly homologous with the nucleotide sequence or the protein sequence of the ThMYB1, ThMYB2, ThR1 and ThR2 genes, and has the same function of controlling the plant anthocyanin synthesis. The highly homologous gene with the function of controlling the anthocyanin synthesis includes an DNA sequence capable of hybridizing with DNA of the sequence as shown in SEQ ID NO: 1, 2, 4, 5, 7, 8, 10 or 11 under a stringent condition, or the nucleotide sequence which codes an amino acid sequence thereof has more than 85% similarity with the protein amino acid sequence as shown in SEQ ID NO: 3, 6, 9 or 12. The 'stringent condition' used in the text are known publicly, for example, hybridizing in a hybridization solution containing 400 mM NaCl, 40 mM PIPES (pH 6.4) and 1 mM EDTA, herein a hybridizing temperature is 53-60 DEG C. preferably, and hybridizing time is 12-16 hours preferably, then washing with washing solution containing 0.5×SSC and 0.1% of SDS, herein a washing temperature is 62-68 DEG C. preferably, and washing time is 15-60 minutes preferably.

The above homologous gene further includes a DNA sequence which has at least 80%, 85%, 90%, 95%, 98% or 99% similarity with an full length of the sequence as shown in SEQ ID NO: 1, 2, 4, 5, 7, 8, 10 or 11 and has the function of regulating the plant anthocyanin biosynthesis, the DNA sequence may be isolated and obtained from any plants. A percentage of the sequence similarity may be obtained by a public biological informatics algorithm, including a Myers and Miller algorithm, a Needleman-Wunsch global alignment method, a Smith-Waterman local alignment method, a Pearson and Lipman similarity search method, and a Karlin and Altschul algorithm. It is publicly known by those skilled in the art.

The disclosure further provides an expression cassette, the expression cassette contains the DNA sequence of the blue-grained gene disclosed by the disclosure, the nucleotide sequence of the blue-grained gene is selected from one of sequences in the following groups:

(a) a nucleotide sequence as shown in SEQ ID NO: 1, 2, 4, 5, 7, 8, 10 or 11;

(b) a nucleotide sequence which encodes an amino acid sequence as shown in SEQ ID NO: 3, 6, 9 or 12;

(c) a DNA sequence capable of hybridizing with DNA of the sequence in (a) or (b) under a stringent condition; or (d) a DNA sequence which has at least 80% (at least 85% preferably) similarity with the sequence in (a)-(c), and has a function of controlling plant anthocyanin synthesis; or (e) a DNA sequence which is complementary to the sequence in any one of (a)-(d).

Specifically, the blue-grained gene in the above expression cassette is further operably connected with a promoter capable of driving the blue-grained gene to express, and the promoter comprises but not limited to a constitutive promoter, an inducible promoter, a tissue-specific promoter, or a spatiotemporal-specific expression promoter. The gene of the constitutive promoter of the disclosure has not tissue and time specificity, and an external factor almost has not effect to exogenous gene expression of the constitutive promoter. The constitutive promoter includes but not limited to a CaMV35S, an FMV35S, an Actin1 promoter, an Ubiquitin promoter and the like. The tissue-specific promoter of the disclosure contains an owned general promoter element, and besides has the features of an enhancer and a silencer, the advantage of this type of the promoter is that the expression of the gene in a plant specific tissue part may be promoted, and the unnecessary expression of the exogenous gene is avoided, so whole energy consumption of the plant is saved. The tissue-specific promoter includes but not limited to an LTP2 seed specific expression promoter, an END2 seed specific expression promoter, an aleurone layer specific expression promoter and the like. The inducible promoter of the disclosure is a promoter which is capable of greatly improving a transcriptional level of the gene under stimulation of some specific physical or chemical signals, the existing isolated inducible promoter includes but not limited to an adversity inducible expression promoter, a light inducible expression promoter, a heat inducible expression promoter, a wound inducible expression promoter, a fungus inducible expression promoter and a symbiotic bacteria inducible expression promoter and the like.

The above expression cassette of the disclosure further includes a screening gene, the screening gene can be used for screening a plant, a plant tissue cell or a vector containing the expression cassette. The screening gene includes but not limited to an antibiotic resistance gene, or a herbicide resistance gene, or a fluorescent protein gene and the like. Specifically, the screening gene includes but not limited to: a chloramphenicol resistance gene, a hygromycin resistance gene, a streptomycin resistance gene, a miramycin resistance gene, a sulfonamides resistance gene, a glyphosate resistance gene, a phosphinothricin resistance gene, a bar gene, a red fluorescence gene DsRED, a mCherry gene, a cyan fluorescent protein gene, a yellow fluorescent protein gene, a luciferase gene, a green fluorescent protein gene and the like.

The disclosure further discloses a method for improving plant anthocyanin content, the method contains co-expressing the ThMYB1 or ThMYB2 gene provided by the disclosure and any one bHLH transcription factor in the tissue and organ of the plant, improving the anthocyanin content in the plant tissue and organ.

The bHLH transcription factor may be Isolated from any one plant, include but not limited to the ThR1 and ThR2 gene provided by the disclosure, and ZmR and ZmB genes from corn (Ahmed N, et al. Transient expression of anthocyanin in developing wheat coleoptile by maize C1 and B-peru regulatory genes for anthocyanin synthesis. Breeding Sci. 2003; 53(1): 29-34.).

The above method for improving the plant anthocyanin content may be used for improving the anthocyanin content of any one tissue or organ of the plant. Specifically, if the anthocyanin content in each tissue of the plant is expected to be improved integrally, the ThMYB1 or ThMYB2 gene and the bHLH transcription factor may be promoted and expressed by using the constitutive promoter. If the anthocyanin content in a certain tissue or organ is expected to be improved, the ThMYB1 or ThMYB2 gene and the bHLH transcription factor may be promoted and expressed by using the specific expression promoter in the tissue or the tissue.

The disclosure further discloses a method for improving plant anthocyanin content, the method contains co-expressing the ThR1 or ThR2 gene provided by the disclosure and any one MYBs transcription factor in the tissue and organ of the plant, improving the anthocyanin content in the plant tissue and organ.

The MYBs transcription factor may be Isolated from any one plant, include but not limited to the ThMYB1 and ThMYB2 gene provided by the disclosure, and an ZmC1 gene from the corn (Ahmed N, et al. Transient expression of anthocyanin in developing wheat coleoptile by maize C1 and B-peru regulatory genes for anthocyanin synthesis. Breeding Sci. 2003; 53(1): 29-34.).

The above method for improving the plant anthocyanin content may be used for improving the anthocyanin content of any one tissue or organ of the plant. Specifically, if the anthocyanin content in each tissue of the plant is expected to be improved integrally, the ThR1 or ThR2 gene and the MYBs transcription factor may be promoted and expressed by using the constitutive promoter. If the anthocyanin content in a certain tissue or organ is expected to be improved, the ThR1 or ThR2 gene and the MYBs transcription factor may be promoted and expressed by using the specific expression promoter in the tissue or the tissue.

The disclosure further provides a visible screening marker gene, the screening marker is capable of, through co-expressing the ThMYB1 or ThMYB2 gene and any one bHLH transcription factor, generating the macroscopic blue screening marker in the tissue and organ of the plant, or co-expressing the ThR1 or ThR2 gene provided by the disclosure and any one MYBs transcription factor in the tissue and organ of the plant, generating the macroscopic blue screening marker in the tissue and organ of the plant.

The screening marker gene disclosed by the disclosure may be used for distinguishing transgenic and non-transgenic materials.

Specifically, the screening marker gene provided by the disclosure may be used as the screening marker in a breeding process of a male sterile line, after a fertility restoring gene, a pollen inactivation gene and the screening marker gene provided by the disclosure are transferred to the male sterile line, the fertility restoring gene may restore fertility of the male sterile line, the pollen inactivation gene may inactivate pollen containing a transformed exogenous gene, namely fertilization is lost, the screening marker gene provided by the disclosure may be used for sorting a transgenic seed or tissue and a non-transgenic seed or tissue, the sorted non-transgenic seed is used as a sterile line for generating a hybridization seed, and the transgenic seed is used as a maintainer line for continuously and stably generating the sterile line.

The screening marker gene provided by the disclosure may be used as the screening marker in a breeding process of a female sterile line, and a female fertility gene, the pollen inactivation gene and the screening marker gene provided by the disclosure are transferred to a female sterile line. Herein, the female fertility gene may restore fertility of a female sterile transforming acceptor material, the pollen inactivation gene may inactivate the pollen containing a transformed exogenous constructing body, namely the fertilization is lost, the screening marker gene provided by the disclosure may be used for sorting the transgenic seed and the non-transgenic seed, the sorted non-transgenic seed is used as the sterile line for generating the hybridization seed, and the transgenic seed is used as the maintainer line for continuously and stably generating the female sterile line and a female sterile maintainer line.

The disclosure further provides the promoter of the blue-grained gene, the promoter has the feature of aleurone layer specific expression, and the nucleotide sequence thereof is as shown in SEQ ID NO: 13, 14, 15 or 16. The SEQ ID NO: 13, 14, 15 or 16 is connected with a reporter gene GUS, a vector is constructed for transforming rice and wheat, and GUS expression activity and an expression mode in the transgenic plant are detected and analyzed, through performing GUS dying analysis on a root, a stem, a leaf, a flower and a seed of the transgenic plant, it is discovered from a result that the promoter provided by the disclosure drives the GUS gene to be expressed in the aleurone layer of the plant seed. It is Indicated that the blue-grained gene promoter SEQ ID NO: 13, 14, 15 or 16 provided by the disclosure is a promoter of aleurone layer specific expression.

The aleurone layer specific expression promoter provided by the disclosure contains the nucleotide sequence as shown in SEQ ID NO: 13, 14, 15 or 16 in a sequence list, or contains the nucleotide sequence which has more than 90% similarity with the nucleotide sequence as shown in SEQ ID NO: 13, 14, 15 or 16, or contains 500 or more than 500 continuous nucleotide fragments derived from the SEQ ID NO: 13, 14, 15 or 16 sequences, and may drive the nucleotide sequence operably connected with the promoter to be expressed in the aleurone layer of the plant seed. An expression vector, a transgenic cell line and host bacteria containing the above sequence and the like belong to a scope of protection of the disclosure. A primer pair for amplifying any one nucleotide fragment of the SEQ ID NO: 13, 14, 15 or 16 promoters disclosed by the disclosure falls within the scope of protection of the disclosure.

The 'promoter' of the disclosure is a DNA control region, the promoter generally contains a TATA box which is capable of guiding RNA polymerase II to start RNA synthesis in a suitable transcription start site of a specific coding sequence. The promoter may further contain other recognition sequences, these recognition sequences are generally positioned at the upstream or 5'-terminal of the TATA box, and generally named as an upstream promoter element, the effect of controlling transcription efficiency is achieved. It is to be noted by those skilled in the art that although the nucleotide sequence in allusion to the promoter region disclosed by the disclosure is identified, other control elements for isolating and identifying the upstream section of the TATA box positioned in the specific promoter section identified by the disclosure also fall within the scope of the disclosure. So, the promoter region disclosed by the text is generally further defined as a control element containing the upstream, for example, these elements, enhancers and the like for controlling tissue expression and a time expression function of the coding sequence. In the same mode, the promoter element which is capable of performing the expression in a target tissue (for example, a male tissue) may be identified and Isolated, the promoter element and other core promoters are used together, to identify the prior expression of the male tissue. The core promoter is the sequence in a minimum limit required by start transcription, for example, the sequence called as the TATA box, the promoter of the coding protein gene generally has the sequence. So, optionally, the aleurone layer specific expression promoter provided by the disclosure may be related and used with own or other source core promoters. The core promoter may be any one known core promoter, for example, a cauliflower mosaic virus 35S or 19S promoter (U.S. Pat. No. 5,352,605), an ubiquitin promoter (U.S. Pat. No. 5,510,474), an IN2 core promoter (U.S. Pat. No. 5,364,780) or a figwort mosaic virus promoter.

A function of the gene promoter of the disclosure may be analyzed by the following method: the promoter sequence is operably connected with the reporter gene, a transformable vector is formed, and the vector is transformed into the plant, in an obtained transgenic offspring, an expression feature thereof is acknowledged through observing an expression condition of the reporter gene in each tissue and organ of the plant; or the above vector is cloned into the expression vector for an transient expression experiment, the function of the promoter or the control region thereof is detected through the transient expression experiment.

Selection of the proper expression vector for testing the function of the promoter or the control region depends on a host or a method for introducing the expression vector into the host, this type of the method is publicly known by those of ordinary skill in the art. About an eucaryon, the region in the vector includes regions for controlling transcription start and controlling processing. These regions are operably connected to the reporter gene, the reporter gene includes YFP, UidA, GUS genes or luciferase. The expression vector containing the presumption control region positioned in the genome fragment may be Introduced into the whole tissue, for example, staged pollen, or introduced into a callus tissue, so functional identification is performed.

In addition, the nucleotide sequence or the fragment or a variant thereof of the aleurone layer specific expression promoter provided by the disclosure and a heterologous nucleotide sequence are assembled in one expression cassette together, and used for the expression in a target plant, more specifically, expression in the seed of the plant. The expression cassette has a proper restriction enzymes analysis site, and is used for Inserting the promotor and the heterologous nucleotide sequence. These expression cassettes may be used for performing genetic operation on any plants, to obtain an expected corresponding phenotype.

The aleurone layer specific expression promoter provided by the disclosure may be used for driving the expression of the following genes, so the transformed plant gains the corresponding phenotype, the gene includes but not limited to a gene related to production increment, a gene for improving a seed nutritional value, a gene for Improving the anthocyanin content, a fluorescent protein gene and the like.

The disclosure further provides an expression cassette, a vector or an engineering strain, the expression cassette, the vector or the engineering strain contains the aleurone layer specific expression promoter SEQ ID NO: 13, 14, 15, or 16 provided by the disclosure, or contains 500 or more than 500 continuous nucleotide fragments derived from the SEQ ID NO: 13, 14, 15 or 16 sequences.

The aleurone layer specific expression promoter provided by the disclosure may be used for the specific expression of the exogenous gene in the seed, so the adverse effect caused by the continuous expression of the exogenous gene in the other tissues of the plant is avoided, and the aleurone layer specific expression promoter has an important disclosure value in plant genetic engineering research.

The nucleotide sequence and the promoter sequence or the expression cassette of the blue-grained gene provided by the disclosure may be inserted into a vector, a plasmid, a yeast artificial chromosome, a bacterial artificial chromosome or any other vectors suitable for transforming in a host cell. Preferable host cell is a bacterial cell, especially the bacterial cell for cloning or storing polynucleotide, or for transforming a plant cell, for example, *Escherichia coli*, *Agrobacterium tumefaciens* and *Agrobacterium rhizogenes*. While the host cell is the plant cell, the expression cassette or the vector may be inserted into a genome of the transformed plant cell. The Insertion may be location or random Insertion.

The methods of transforming the nucleotide sequence, the vector or the expression cassette into the plant or introducing the plant or transforming the plant in the disclosure are conventional transgenic methods through which the nucleotide sequence, the vector or the expression cassette is transformed into the acceptor cell or the acceptor plant. Any transgenic methods known by those skilled in the plant biology art may be used for transforming a recombinant expression vector into the plant cell, so the transgenic plant of the disclosure is produced. The transformation method may Include direct and indirect transformation methods. The suitable direct method includes DNA uptake induced by polyethylene glycol, transformation mediated by a lipidosome, import by using a gene gun, electroporation, and micro-injection. The transformation method also includes an *Agrobacterium*-mediated plant transformation method and the like.

Compared with the related art, the disclosure has the following beneficial effects: the disclosure provides a blue-grained gene and a promoter thereof, the blue-grained gene may improve the content of anthocyanin in the plant, because the anthocyanin has an anti-oxidation function, in the age that environmental pollution is Intensified and people pursue healthy life increasingly, discovery of the anthocyanin synthesis related gene undoubtedly increases a nutritional value and a medical value of the plant edible part. At the same time, the blue-grained gene may be further used as the screening marker while the anthocyanin content of the plant is improved, a process of eliminating the screening marker in the transgenic process is eliminated, time and steps of transgenic bioengineering are saved, and the blue-grained gene has the Important disclosure value in practical production disclosure.

REFERENCES

Zhou K, Wang S, Feng Y, Liu Z, Wang G. The 4E-system of producing hybrid wheat. Crop Sci. 2006; 46(1): 250-255.
Li Zhengsheng, Mu sumel. Blue-grained monomer wheat research (one)[J]. Genetics, 1982(6): 15.
Zheng Q., Li B., Mu S., Zhou H., Li Z. (2006). Physical mapping of the blue-grained gene(s) from *Thinopyrum ponticum* by GISH and FISH in a set of translocation lines with different seed colors in wheat. Genome 49, 1109-1114.
Dubcovsky, J., Luo, M. C., Zhong, G. Y., Bransteitter, R., Desai, A., Kilian, A., et al. (1996). Genetic map of diploid wheat, *Triticum monococcum* L., and its comparison with maps of *Hordeum vulgare* L. Genetics 143, 983-999.
Himi, E., and Noda, K. (2005). Red grain colour gene (R) of wheat is a Myb-type transcription factor. Euphytica 143, 239-242.
Khlestkina, E. K. Genes determining coloration of different organs in wheat. Russ. J. Genet. Appl. Res. 2013, 3, 54-65.
Shoeva, O. Y., Gordeeva, E. L., and Khlestkina, E. K. (2014). The regulation of anthocyanin synthesis in the wheat pericarp. Molecules 19, 20266-20279.

Gong jia, Xue jing, Zhang xiaodong, 2011. Control gene research progress in plant anthocyanin synthetic route. Biotechnology Progress 1(6): 381-390.

Ahmed N, Maekawa M, Utsugi S, Himi E, Ablet H, Rikiishi K, et al. Transient expression of anthocyanin in developing wheat coleoptile by maize C1 and B-peru regulatory genes for anthocyanin synthesis. Breeding Sci. 2003; 53(1): 29-34.

The drawings are used for providing further understanding to the disclosure, and form a part of the disclosure, and are used for explaining the disclosure with the following specific implementation modes, but not intended to limit the disclosure.

DETAILED DESCRIPTION OF THE EMBODIMENTS

The embodiments of the disclosure are described below in detail, the embodiments are implemented by using the technical scheme of the disclosure as a precondition, and detailed implementation and specific operation process are provided, but the scope of protection of the disclosure is not limited to the following embodiments.

Embodiment 1. Cloning of Blue-Grained Genes

Figure 1:
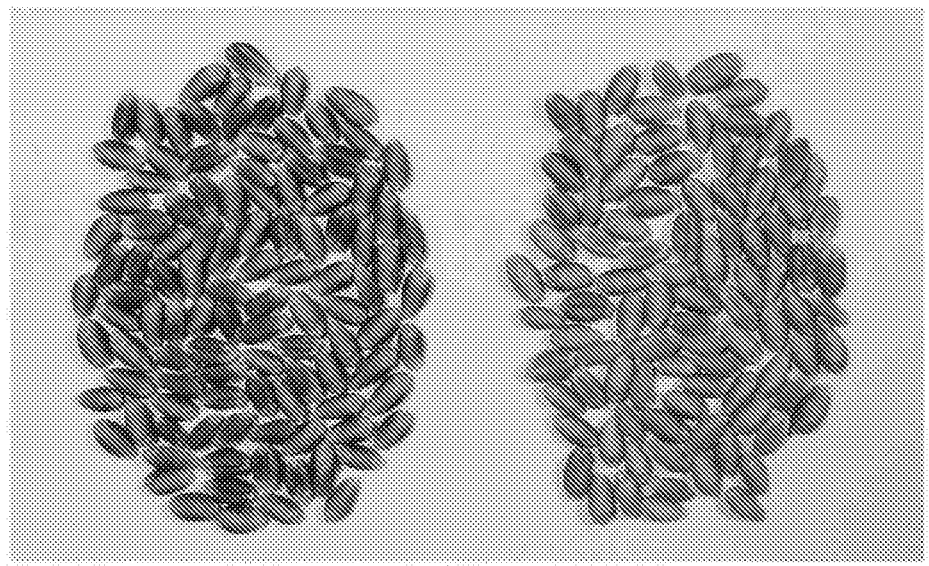
FIG. 1 shows grain colors of blue-grained wheat and white grain wheat. A left diagram shows deep blue grains of the blue-grained wheat 3114BB, and a right diagram shows white grains of the parent white grain wheat 3114 thereof.

In order to clone the blue-grained genes in wheat, which is derived from 4Ag chromosome of *Thinopyrum ponticum*, the disclosure performs differential expression analysis (as shown in FIG. 1) between blue-grained and white grain wheat, theoretically, differential expression genes between the blue-grained and white grain wheat contain two types: 1) genes expressed by the 4Ag chromosome of *Thinopyrum ponticum*, which contains the blue-grained gene expected to be cloned by the disclosure; and 2) downstream genes caused by the expression of the 4Ag chromosome of *Thinopyrum ponticum*, and these genes are from the wheat genome. The disclosure expects to analyze and obtain the blue-grained gene in 1). the blue-grained wheat 3114BB and parent white grain wheat 3114 are selected as material, thereof, because the blue color of the aleurone layer appears in about 20 days after anthesis, after about 25 days, the grain aleurone layer is totally changed into the blue, so the disclosure dissected the aleurone layer sample in 25 days after anthesis, two repeats of each of blue-grained and white grain materials are taken, and respectively marked as blue 1, blue 2, white 1 and white 2, RNA is extracted and high-throughput sequencing is performed (PE125), and 9 Gb of data was obtained from each sample.

Because the published wheat reference genome only covers 61% of the whole genome, the gene annotation is incomplete and the scaffolds are fragmented, the target genes may not be found out by direct sequence alignment and differential gene expression analysis. The disclosure adopts a three-step exclusive method, firstly a double-end sequence accurately aligned to the wheat reference genome is excluded, secondly the remaining double-end short sequences are de novo assembled and the high expression genes in the white grain wheat are excluded, and finally the genes irrelated with anthocyanin metabolism are excluded from the differential expression genes in comply with conditions.

Through the above analysis, the disclosure obtains 139 differential expression genes in a non-wheat reference genome, herein 35 genes are high expressed in the blue-grained wheat, and almost not expressed in the white grain wheat, by gene function annotation analysis, after the genes irrelated with the anthocyanin metabolism are excluded, there are only two target genes encoding a MYB protein and a bHLH protein, respectively, the disclosure names the two target genes as ThMYB1 and ThR1. On the basis of the cDNA sequences of ThMYB1 and ThR1, the disclosure is capable of, through PCR amplification, obtaining the genomic sequences of the two genes, in this process, the disclosure discovered that another highly homologous sequence is obtained in the PCR products of both ThMYB1 and ThR1, so the disclosure clones two homologous sequences and respectively names the sequences as ThMYB2 and ThR2. Through genome walking technology, the disclosure respectively obtains promoter sequences and terminator sequences of the four genes.

Herein, a genome nucleotide sequence of the ThMYB1 gene from an initiation codon to a termination codon is as shown in SEQ ID NO: 1, the nucleotide sequence of a coding sequence (CDS) thereof is as shown in SEQ ID NO: 2, and an amino acid sequence coded by the CDS thereof is as shown in SEQ ID NO: 3, the promoter sequence thereof is as shown in SEQ ID NO: 13, and the terminator sequence thereof is shown in SEQ ID NO: 17. Herein the genome nucleotide sequence of the ThMYB2 gene from the initiation codon to the termination codon is as shown in SEQ ID NO: 4, the nucleotide sequence of the coding sequence (CDS) thereof is as shown in SEQ ID NO: 5, and the amino acid sequence coded by the CDS thereof is as shown in SEQ ID NO: 6, the promoter sequence thereof is as shown in SEQ ID NO: 14, and the terminator sequence thereof is shown in SEQ ID NO: 18. Herein the genome nucleotide sequence of the ThR1 gene from the initiation codon to the termination codon is as shown in SEQ ID NO: 7, the nucleotide sequence of the coding sequence (CDS) thereof is as shown in SEQ ID NO: 8, and the amino acid sequence coded by the CDS thereof is as shown in SEQ ID NO: 9, the promoter sequence thereof is as shown in SEQ ID NO: 15, and the terminator sequence thereof is shown in SEQ ID NO: 19. Herein the genome nucleotide sequence of the ThR2 gene from the initiation codon to the termination codon is as shown in SEQ ID NO: 10, the nucleotide sequence of the coding sequence (CDS) thereof is as shown in SEQ ID NO: 11, and the amino acid sequence coded by the CDS thereof is as shown in SEQ ID NO: 12, the promoter sequence thereof is as shown in SEQ ID NO: 16, and the terminator sequence thereof is shown in SEQ ID NO: 20.

Figure 2:
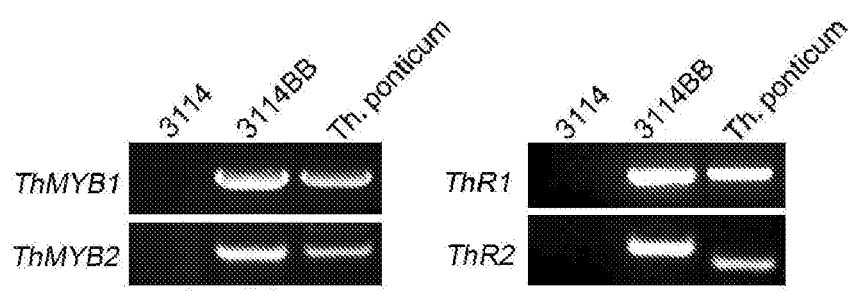
FIG. 2 shows sources of the four blue-grained genes ThMYB1, ThMYB2, ThR1 and ThR2 verified by genome RCR. A left diagram is an agarose gel electrophoresis diagram of PCR products of the ThMYB1 and ThMYB2 genes, and a right diagram is an agarose gel electrophoresis diagram of PCR products of the ThR1 and ThR2 genes. The four genes are not detected in the genome of the white grain wheat 3114, but detected in the genomes of the blue-grained wheat 3114BB and *Thinopyrum ponticum*.
Figure 3:
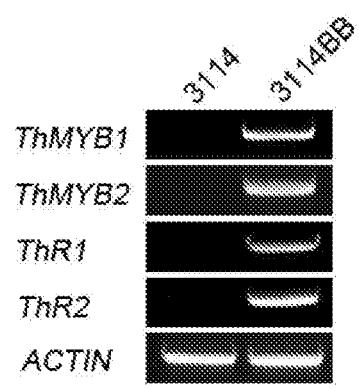
FIG. 3 shows sources of the four blue-grained genes verified by semi-quantitative RT-PCR. An agarose gel electrophoresis diagram of a PCR product shows that the expression of the four genes is not detected in cDNA of the white grain wheat 3114, but the expression of the four genes may be detected in the cDNA of the blue-grained wheat 3114BB, herein ACTIN is a housekeeping gene.

The disclosure verifies sources of the four genes using genome PCR and semi-quantitative RT-PCR. The genome PCR result shows that: in the white grain wheat 3114 genome, there are no ThMYB1, ThMYB2, ThR1 and ThR2 detected, but in the blue-grained wheat 3114BB and *Thinopyrum ponticum* genome, the four genes could be detected, it is indicated that the four genes are really derived from the 4Ag chromosome of *Thinopyrum ponticum* instead of the common wheat (as shown in FIG. 2). A semi-quantitative RT-PCR result in cDNA of 25 DAP aleurone layer tissue also shows that ThMYB1, ThMYB2, ThR1 and ThR2 are not expressed in the aleurone layer of white grain wheat, and only highly expressed in the aleurone layer of blue-grained wheat (as shown in FIG. 3). The above results show that the four genes (ThMYB1, ThMYB2, ThR1 and ThR2) are derived from the 4Ag chromosome of *Thinopyrum ponticum*, and highly expressed in the aleurone layer of blue-grained wheat, it may be the blue-grained genes found by the disclosure.

Embodiment 2. Expression Pattern of the Blue-Grained Genes

Figure 4:
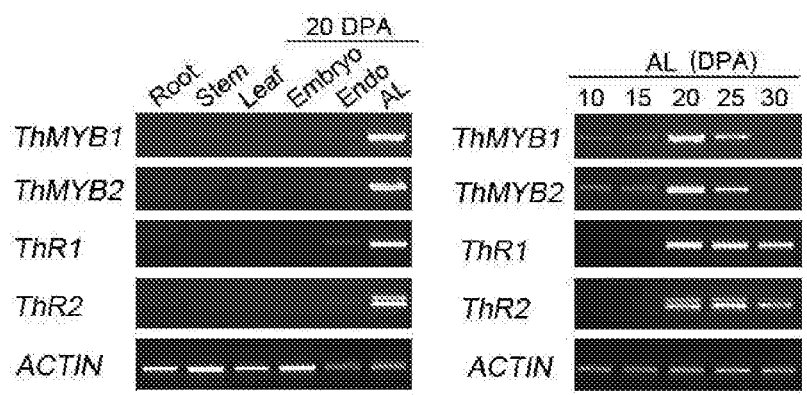
FIG. 4 shows the expression pattern of the four blue-grained genes in the blue-grained wheat 3114BB verified by semi-quantitative RT-PCR. A left diagram Is an agarose gel electrophoresis diagram of PCR products of the blue-grained genes in different plant organs or tissues, and a right diagram is an agarose gel electrophoresis diagram of PCR products of the blue-grained genes in each development stage of the aleurone layer, herein the ACTIN Is the housekeeping gene. The expression of the four genes is not detected in cDNA of root, stem, leaf, embryo and endosperm, but the high expression of the four genes may be detected in the aleurone layer, and expression level of the different blue-grained genes in different numbers of growth days of the aleurone layer are not same completely. DPA is days post anthesis, namely 'a number of days after anthesis'.

The disclosure uses a semi-quantitative RT-PCR to verify the expression pattern of the four genes as shown in FIG. 4.

Firstly, the four genes are not detected in vegetative organs of the blue-grained wheat 3114BB, such as root, stem and leaf, in different tissues of 20 DAP (days post anthesis) seeds, the four genes are specifically expressed in aleurone layer, but not in embryo and endosperm, this indicates that the four genes are aleurone layer-specific genes, and the promoters of the four genes thereof are aleurone layer-specific promoters. Further, the disclosure analyzes the expression pattern of the ThMYB1, ThMYB2, ThR1 and ThR2 in the aleurone layer of blue-grained wheat seed in different days post anthesis, it is discovered that the expression patterns of two MYB and two bHLH genes are not same completely: ThMYB1 and ThMYB2 are expressed in a very low level in 10 DPA and 15 DPA aleurone layer, and suddenly highly expressed in 20 DPA, after that gradually reduced in 25 DPA and 30 DPA; ThR1 and ThR2 are not detected in 10 DPA and 15 DPA aleurone layer, and continuously highly expressed from 20 DPA to 30 DPA. The above result shows that ThMYB1, ThMYB2, ThR1 and ThR2 are the wheat aleurone layer-specific genes, and the expression patterns thereof display spatiotemporal specificity.

The promoter sequences SEQ ID NO: 13, 14, 15 and 16 of the above four genes drive a GUS gene to perform functional verification in plants of rice, maize and the like, it is discovered that all of the above promoters drive the GUS to be specifically expressed in the aleurone layer, it is indicated that the above promoters provided by the disclosure are aleurone layer-specific promoters.

Figure 5:
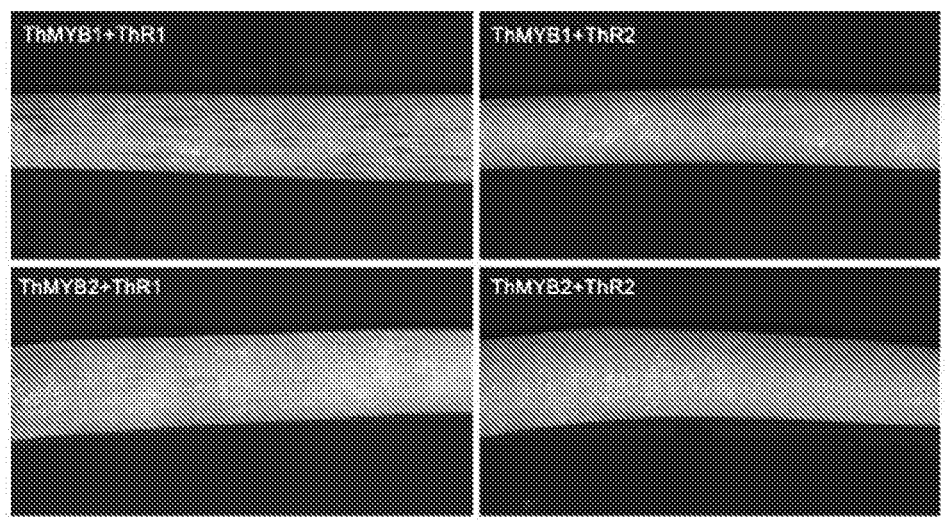
FIG. 5 shows that transient expression by particle bombardment to verify that the four blue-grained genes may induce red anthocyanin spots in wheat coleoptiles. The different combinations of the four blue-grained genes are respectively co-transformed into the wheat coleoptiles. After cultured for 16 hours in an illumination incubator, the wheat coleoptiles were observed using a microscope and the results showed that ThMYB1+ThR1 combination and ThMYB2+ThR1 combination may induce most of cells to generate red anthocyanin spots, ThMYB1+ThR2 combination only induces a small number of the cells to generate the anthocyanin, and ThMYB2+ThR2 combination may not induce to generate the anthocyanin.

Embodiment 3. Experiment of Transient Expression in Wheat Coleoptile by Particle Bombardment Previous research has proved that co-transformation of a corn MYB family transcription factor C1 and a bHLH family transcription factor B1 in wheat coleoptile by particle bombardment may induce red anthocyanin spots in wheat coleoptiles (Ahmed N, Maekawa M, Utsugi S, Himi E, Ablet H, Rikiishi K, et al. Transient expression of anthocyanin in developing wheat coleoptile by maize C1 and B-peru regulatory genes for anthocyanin synthesis. Breeding Sci. 2003; 53(1): 29-34). In order to verify whether two MYB genes and two bHLH genes obtained by the disclosure have the same function, vectors for transient expression by particle bombardment are constructed with the four genes by the disclosure. Firstly a NOS terminator is cloned into a pEASY-T1 simple (TransGen corporation) vector, and the open reading frames of ThMYB1, ThMYB2, ThR1 and ThR2 are inserted in front of the NOS, finally an Ubi (Ubiquitin) promoter from maize is inserted in front of the open reading frame by in-fusion system to drive gene expression, and forming four vectors of Ubi::ThMYB1, Ubi::ThMYB2, Ubi::ThR1 and Ubi::ThR2. According to previous reference (Ahmed et al, 2003), the transforming vectors of MYB and bHLH genes are combined in pairs, namely four combinations of ThMYB1+ThR1, ThMYB1+ThR2, ThMYB2+ThR1 and ThMYB2+ThR2 are co-transformed to the wheat coleoptile. after incubated for 16 hours in an illumination incubator, the wheat coleoptiles are observed under a microscope and photographed, as shown in FIG. 5: the combinations of ThMYB1+ThR1 and ThMYB2+ThR1 may induce generation of red anthocyanin, and ThMYB1+ThR2 may also induce formation of anthocyanin.

Embodiment 4. Constructs for Plant Transformation

Figure 6:
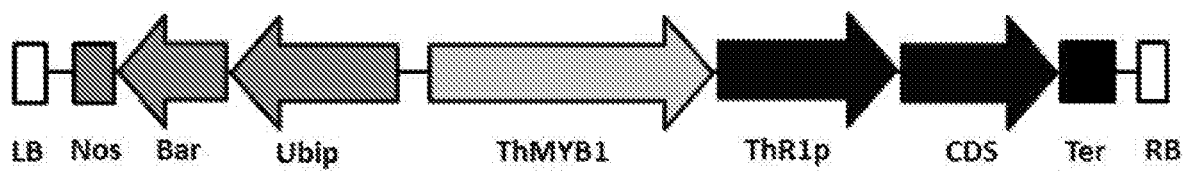
FIG. 6 shows a construction schematic diagram for a plant transformation vector of a wheat transgenic experiment. Herein, LB and RB are left and right borders of T-DNA; expression of a Bar resistance gene is driven by an Ubip (a promoter of a Ubi gene), and terminated by a Nos terminator; and expression of the ThMYB1 and ThR1 genes is respectively controlled by own promoter and terminator.

In order to further verify that ThMYB1, ThMYB2, ThR1 and ThR2 are blue-grained genes, the disclosure selects two genes of ThMYB1 and ThR1 to construct a stable transforming vector for wheat transgenic experiment. A binary expression vector pCAMBIA1300 is used as a framework, firstly a plant resistance screening cassette (a hygromycin driven by 35S) on the pCAMBIA1300 is replaced by a Bar resistance gene expression cassette driven by an Ubi promotor from pAHC20 vector. On this basis, 3215 bp ThMYB1 genomic sequences (containing a 1952 bp promoter sequence, a 822 bp genomic sequence and a 441 bp terminator sequence) and 4422 bp ThR1 genomic sequences (containing a 2084 bp promoter sequence, a 1720 bp CDS sequence and a 618 bp terminator sequence) are inserted in a multi-cloning site, so a vector for plant transformation (as shown in FIG. 6) is formed.

Embodiment 5. Acquisition of Transgenic Blue-Grained Wheat

Figure 7:
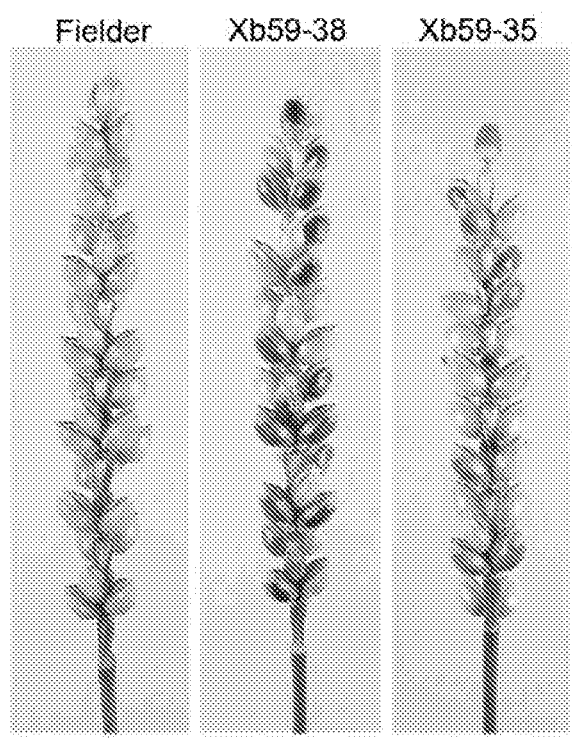
FIG. 7 shows grain color of a $T_1$-generation plant of ThMYB1+ThR1 transgenic wheat under the background of wheat variety fielder that is obtained by using *Agrobacterium tumefaciens* mediated transformation. A left diagram is the white grain of the non-transgenic wheat variety fielder, a middle diagram is a strain of a deep blue-grained in the $T_1$-generation transgenic plant, and a right diagram is a strain of a wathet blue-grained in the $T_1$-generation transgenic plant.

The plant expression vector constructed in the embodiment 4 is transformed into an *Agrobacterium* strain C58C1 by electroporation method. The vector Is transformed to wheat variety fielder by use of *Agrobacterium*-mediated wheat transformation system, and 96 transgenic positive $T_0$-generation plants are obtained. The wheat grain color was observed when $T_0$-generation plants were harvested, it is discovered that a part of the plants bare deep blue grains, and a part of the plants bare wathet blue grains (accounting for about 34%), and a specific result is as shown in FIG. 7. The transgenic result shows that the co-expression of ThMYB1 and ThR1 in plant could increase the anthocyanin content, and the ThMYB1, ThMYB2, ThR1 and ThR2 provided by the disclosure are the blue-grained genes in the wheat.

Embodiment 6. Functional Verification of Blue-Grained Gene in Rice, *Arabidopsis* and Maize ThMYB1 or ThMYB2 gene provided by the disclosure is combined with ThR1, ThR2, ZmR and ZmB genes in pairs according to a mode of one MYB gene plus one HLH gene, and transferred into the plants of rice, *Arabidopsis* and maize and the like and co-expressed, it is discovered that the gene has the same function of improving anthocyanin content in the plant.

What is claimed is:

1. An expression cassette, wherein the expression cassette comprises the blue-grained gene, and a nucleotide sequence of the blue-grained gene is selected from the group consisting of:
   (a) a nucleotide sequence as shown in SEQ ID NO: 1, 2, 4 or 5; or
   (b) a nucleotide sequence which codes an amino acid sequence as shown in SEQ ID NO: 3 or 6.

2. The expression cassette of claim 1, wherein the blue-grained gene is operably connected with a promoter capable of driving expression of the blue-grained gene, and the promoter is but not limited to a constitutive promoter, an inducible promoter, a tissue-specific promoter, or a spatiotemporal-specific expression promoter.

3. A method for improving plant anthocyanin content, comprising: co-expressing a MYB transcription factor and a bHLH transcription factor in tissue or organ of a plant, wherein the MYB transcription factor is a ThMYB1 or ThMYB2 gene, and the nucleotide sequence is selected from the group consisting of:
   (a) a nucleotide sequence as shown in SEQ ID NO: 1, 2, 4, or 5;
   (b) a nucleotide sequence which codes an amino acid sequence as shown in SEQ ID NO: 3 or 6:
   the bHLH transcription factor comprises a ThR1, ThR2, ZmR or ZmB gene.

4. A method for improving plant anthocyanin content, comprising: co-expressing the expression cassette of claim 1 and any one bHLH transcription factor in tissue or organ of a plant;
   and wherein the bHLH transcription factor comprises a ThR1, ThR2, ZmR or ZmB gene.

5. A method for improving plant anthocyanin content, comprising: co-expressing the expression cassette of claim 2 and any one bHLH transcription factor in tissue or organ of a plant;
   and wherein the bHLH transcription factor comprises a ThR1, ThR2, ZmR or ZmB gene.

6. The method of claim 3, wherein the nucleotide sequences of the ThR1 and ThR2 genes are selected from the group consisting of:
   (a) a nucleotide sequence as shown in SEQ ID NO: 7, 8, 10, or 11; or
   (b) a nucleotide sequence which codes an amino acid sequence as shown in SEQ ID NO: 9 or 12.

* * * * *